(12) United States Patent
Andrews et al.

(10) Patent No.: US 9,387,131 B2
(45) Date of Patent: Jul. 12, 2016

(54) APPARATUS AND METHOD FOR MINIMIZING WASTE AND IMPROVING QUALITY AND PRODUCTION IN WEB PROCESSING OPERATIONS BY AUTOMATED THREADING AND RE-THREADING OF WEB MATERIALS

(75) Inventors: Robert E Andrews, Sheboygan, WI (US); Jeff W Fritz, Plymouth, WI (US); Jason Hohm, Sheboygan Falls, WI (US); Song Sayaovong, Glendale, WI (US); Peter Strains, Sheboygan Falls, WI (US); Donald R Dodelin, Woodstock, GA (US)

(73) Assignee: Curt G. Joa, Inc., Sheboygan Falls, WI (US)

( * ) Notice: Subject to any disclaimer, the term of this patent is extended or adjusted under 35 U.S.C. 154(b) by 1008 days.

(21) Appl. No.: 13/160,932

(22) Filed: Jun. 15, 2011

(65) Prior Publication Data
US 2012/0159753 A1    Jun. 28, 2012

Related U.S. Application Data

(63) Continuation-in-part of application No. 11/880,261, filed on Jul. 20, 2007, now Pat. No. 8,398,793.

(60) Provisional application No. 61/400,318, filed on Jul. 26, 2010.

(51) Int. Cl.
*B65H 20/14*    (2006.01)
*A61F 13/15*    (2006.01)
(Continued)

(52) U.S. Cl.
CPC ........... *A61F 13/15772* (2013.01); *A61F 13/15* (2013.01); *A61F 13/15577* (2013.01);
(Continued)

(58) Field of Classification Search
CPC .............................................. B65H 2301/52202
USPC ....................................................... 226/91, 92
See application file for complete search history.

(56) References Cited

U.S. PATENT DOCUMENTS

| 35,145 A | 1/1873 | Murphy |
| 2,933,353 A | 2/1884 | Purvis |

(Continued)

FOREIGN PATENT DOCUMENTS

| BE | 1007854 | 11/1995 |
| CA | 1146129 | 5/1983 |

(Continued)

OTHER PUBLICATIONS

International Search Report dated Nov. 3, 2011 regarding EP Application No. 11250672.0, 4 pages.

(Continued)

*Primary Examiner* — William E Dondero
(74) *Attorney, Agent, or Firm* — Ryan Kromholz & Manion, S.C.

(57) ABSTRACT

Apparatus and methods are provided to minimize waste and improve quality and production in web processing operations. A first non-elastomeric layer is bonded with an elastomeric layer, and to a second non-elastomeric layer. The apparatus and methods provide defect detection in the elastomeric layer and triggers an unthreading/rethreading sequence. Web defect detection may be provided by way of at least one visual inspection station. If defects are detected in the elastic layer, the resulting products may be culled.

1 Claim, 17 Drawing Sheets

(51) Int. Cl.
  *B65H 39/16* (2006.01)
  *B65H 20/34* (2006.01)
  *B65H 20/32* (2006.01)
  *B65H 23/24* (2006.01)

(52) U.S. Cl.
  CPC .......... *A61F13/15699* (2013.01); *B65H 20/14* (2013.01); *B65H 20/32* (2013.01); *B65H 20/34* (2013.01); *B65H 23/24* (2013.01); *B65H 39/16* (2013.01); *B65H 2301/52202* (2013.01)

(56) References Cited

U.S. PATENT DOCUMENTS

| | | | |
|---|---|---|---|
| 312,257 A | 2/1885 | Cotton et al. | |
| 410,123 A | 8/1889 | Stilwell | |
| 432,742 A | 7/1890 | Stanley | |
| 643,821 A | 2/1900 | Howlett | |
| 1,393,524 A | 10/1921 | Grupe | |
| 1,431,315 A | 10/1922 | Le Moine | |
| 1,605,842 A | 11/1926 | Jones | |
| 1,629,681 A * | 5/1927 | Cram | 100/162 R |
| 1,686,595 A | 10/1928 | Belluche | |
| 1,957,651 A | 5/1934 | Joa | |
| 2,009,857 A | 7/1935 | Potdevin | |
| 2,054,832 A | 9/1936 | Potdevin | |
| 2,117,432 A | 5/1938 | Linscott | |
| 2,128,746 A | 8/1938 | Joa | |
| 2,131,808 A | 10/1938 | Joa | |
| 2,164,408 A | 7/1939 | Joa | |
| 2,167,179 A | 7/1939 | Joa | |
| 2,171,741 A | 9/1939 | Cohn et al. | |
| 2,213,431 A | 9/1940 | Joa | |
| 2,254,290 A | 9/1941 | Joa | |
| 2,254,291 A | 9/1941 | Joa | |
| 2,282,477 A | 5/1942 | Joa | |
| 2,286,096 A | 6/1942 | Joa | |
| 2,296,931 A | 9/1942 | Joa | |
| 2,304,571 A | 12/1942 | Joa | |
| 2,324,930 A | 7/1943 | Joa | |
| 2,345,937 A | 4/1944 | Joa | |
| 2,466,240 A | 4/1949 | Joa | |
| 2,481,929 A | 9/1949 | Joa | |
| 2,510,229 A | 6/1950 | Joa | |
| 2,540,844 A | 2/1951 | Strauss | |
| 2,584,002 A | 1/1952 | Elser et al. | |
| 2,591,359 A | 4/1952 | Joa | |
| 2,618,816 A | 11/1952 | Joa | |
| 2,627,859 A | 2/1953 | Hargrave | |
| 2,695,025 A | 11/1954 | Andrews | |
| 2,702,406 A | 2/1955 | Reed | |
| 2,721,554 A | 10/1955 | Joa | |
| 2,730,144 A | 1/1956 | Joa | |
| 2,772,611 A | 12/1956 | Heywood | |
| 2,780,253 A | 2/1957 | Joa | |
| 2,785,609 A | 3/1957 | Billeb | |
| 2,788,786 A | 4/1957 | Dexter | |
| 2,811,905 A | 11/1957 | Kennedy, Jr. | |
| 2,828,745 A | 4/1958 | Deutz | |
| 2,839,059 A | 6/1958 | Joa | |
| 2,842,169 A | 7/1958 | Joa | |
| 2,851,934 A | 9/1958 | Heywood | |
| 2,875,724 A | 3/1959 | Joa | |
| 2,890,700 A | 6/1959 | Lonberg-Holm | |
| 2,913,862 A | 11/1959 | Sabee | |
| 2,939,461 A | 6/1960 | Joa | |
| 2,939,646 A | 6/1960 | Stone | |
| 2,960,143 A | 11/1960 | Joa | |
| 2,990,081 A | 6/1961 | De Neui et al. | |
| 2,991,739 A | 7/1961 | Joa | |
| 3,016,207 A | 1/1962 | Comstock, III | |
| 3,016,582 A | 1/1962 | Joa | |
| 3,017,795 A | 1/1962 | Joa | |
| 3,020,687 A | 2/1962 | Joa | |
| 3,021,135 A | 2/1962 | Joa | |
| 3,024,957 A | 3/1962 | Pinto | |
| 3,053,427 A | 9/1962 | Wasserman | |
| 3,054,516 A | 9/1962 | Joa | |
| 3,069,982 A | 12/1962 | Heywood et al. | |
| 3,086,253 A | 4/1963 | Joa | |
| 3,087,689 A | 4/1963 | Heim | |
| 3,089,494 A | 5/1963 | Schwartz | |
| 3,091,408 A | 5/1963 | Schoeneman | |
| 3,114,994 A | 12/1963 | Joa | |
| 3,122,293 A | 2/1964 | Joa | |
| 3,128,206 A | 4/1964 | Dungler | |
| 3,203,419 A | 8/1965 | Joa | |
| 3,230,955 A | 1/1966 | Joa | |
| 3,268,954 A | 8/1966 | Joa | |
| 3,288,037 A | 11/1966 | Burnett | |
| 3,289,254 A | 12/1966 | Joa | |
| 3,291,131 A | 12/1966 | Joa | |
| 3,301,114 A | 1/1967 | Joa | |
| 3,318,608 A | 5/1967 | Smrekar | |
| 3,322,589 A | 5/1967 | Joa | |
| 3,336,847 A | 8/1967 | Johnson | |
| 3,342,184 A | 9/1967 | Joa | |
| 3,356,092 A | 12/1967 | Joa | |
| 3,360,103 A | 12/1967 | Joa | |
| 3,391,777 A | 7/1968 | Joa | |
| 3,454,442 A | 7/1969 | Heller, Jr. | |
| 3,463,413 A | 8/1969 | Smith | |
| 3,470,848 A | 10/1969 | Dreher | |
| 3,484,275 A | 12/1969 | Lewicki, Jr. | |
| 3,502,322 A | 3/1970 | Cran | |
| 3,521,639 A | 7/1970 | Joa | |
| 3,526,563 A | 9/1970 | Schott, Jr. | |
| 3,538,551 A | 11/1970 | Joa | |
| 3,540,641 A | 11/1970 | Besnyo | |
| 3,575,170 A | 4/1971 | Clark | |
| 3,607,578 A | 9/1971 | Berg et al. | |
| 3,635,462 A | 1/1972 | Joa | |
| 3,656,741 A | 4/1972 | Macke et al. | |
| 3,666,611 A | 5/1972 | Joa | |
| 3,673,021 A | 6/1972 | Joa | |
| 3,685,818 A | 8/1972 | Burger et al. | |
| 3,728,191 A | 4/1973 | Wierzba et al. | |
| 3,751,224 A | 8/1973 | Wackerle | |
| 3,758,102 A | 9/1973 | Munn et al. | |
| 3,772,120 A | 11/1973 | Radzins | |
| 3,776,798 A | 12/1973 | Milano | |
| 3,796,360 A | 3/1974 | Alexeff | |
| 3,811,987 A | 5/1974 | Wilkinson et al. | |
| 3,816,210 A | 6/1974 | Aoko et al. | |
| 3,847,710 A | 11/1974 | Blomqvist et al. | |
| 3,854,917 A | 12/1974 | McKinney et al. | |
| 3,883,389 A | 5/1975 | Schott, Jr. | |
| 3,888,400 A | 6/1975 | Wiig | |
| 3,901,238 A | 8/1975 | Geller et al. | |
| 3,903,768 A | 9/1975 | Amberg et al. | |
| 3,904,147 A | 9/1975 | Taitel et al. | |
| 3,918,698 A | 11/1975 | Coast | |
| 3,960,646 A | 6/1976 | Wiedamann | |
| 3,988,194 A | 10/1976 | Babcock et al. | |
| 3,991,994 A | 11/1976 | Farish | |
| 4,002,005 A | 1/1977 | Mueller et al. | |
| 4,003,298 A | 1/1977 | Schott, Jr. | |
| 4,009,814 A | 3/1977 | Singh | |
| 4,009,815 A | 3/1977 | Ericson et al. | |
| 4,053,150 A | 10/1977 | Lane | |
| 4,056,919 A | 11/1977 | Hirsch | |
| 4,081,301 A | 3/1978 | Buell | |
| 4,090,516 A | 5/1978 | Schaar | |
| 4,094,319 A | 6/1978 | Joa | |
| 4,103,595 A | 8/1978 | Corse | |
| 4,106,974 A | 8/1978 | Hirsch | |
| 4,108,584 A | 8/1978 | Radzins et al. | |
| 4,136,535 A | 1/1979 | Audas | |
| 4,141,193 A | 2/1979 | Joa | |
| 4,141,509 A | 2/1979 | Radzins | |
| 4,142,626 A | 3/1979 | Bradley | |
| 4,157,934 A | 6/1979 | Ryan et al. | |
| 4,165,666 A | 8/1979 | Johnson et al. | |
| 4,168,776 A | 9/1979 | Hoeboer | |
| 4,171,239 A | 10/1979 | Hirsch et al. | |

(56) References Cited

U.S. PATENT DOCUMENTS

| | | |
|---|---|---|
| 4,205,679 A | 6/1980 | Repke et al. |
| 4,208,230 A | 6/1980 | Magarian |
| 4,213,356 A | 7/1980 | Armitage |
| 4,215,827 A | 8/1980 | Roberts et al. |
| 4,222,533 A | 9/1980 | Pongracz |
| 4,223,822 A | 9/1980 | Clitheroe |
| 4,231,129 A | 11/1980 | Winch |
| 4,236,955 A | 12/1980 | Prittie |
| 4,275,510 A | 6/1981 | George |
| 4,284,454 A | 8/1981 | Joa |
| 4,307,800 A | 12/1981 | Joa |
| 4,316,756 A | 2/1982 | Wilson |
| 4,325,519 A | 4/1982 | McLean |
| 4,342,206 A | 8/1982 | Rommel |
| 4,364,787 A | 12/1982 | Radzins |
| 4,374,576 A | 2/1983 | Ryan |
| 4,379,008 A | 4/1983 | Gross et al. |
| 4,394,898 A | 7/1983 | Campbell |
| 4,411,721 A | 10/1983 | Wishart |
| 4,452,597 A | 6/1984 | Achelpohl |
| 4,492,608 A | 1/1985 | Hirsch et al. |
| 4,501,098 A | 2/1985 | Gregory |
| 4,508,528 A | 4/1985 | Hirsch et al. |
| 4,522,853 A | 6/1985 | Szonn et al. |
| 4,543,152 A | 9/1985 | Nozaka |
| 4,551,191 A | 11/1985 | Kock et al. |
| 4,586,199 A | 5/1986 | Birring |
| 4,589,945 A | 5/1986 | Polit |
| 4,603,800 A | 8/1986 | Focke et al. |
| 4,608,115 A | 8/1986 | Schroth et al. |
| 4,610,097 A * | 9/1986 | Kotitschke et al. ............. 34/418 |
| 4,610,681 A | 9/1986 | Strohbeen et al. |
| 4,610,682 A | 9/1986 | Kopp |
| 4,614,076 A | 9/1986 | Rathemacher |
| 4,619,357 A | 10/1986 | Radzins et al. |
| 4,634,482 A | 1/1987 | Lammers |
| 4,641,381 A | 2/1987 | Heran et al. |
| 4,642,150 A | 2/1987 | Stemmler |
| 4,642,839 A | 2/1987 | Urban |
| 4,650,530 A | 3/1987 | Mahoney et al. |
| 4,663,220 A | 5/1987 | Wisneski et al. |
| 4,672,705 A | 6/1987 | Bors et al. |
| 4,675,016 A | 6/1987 | Meuli et al. |
| 4,675,062 A | 6/1987 | Instance |
| 4,675,068 A | 6/1987 | Lundmark |
| 4,686,136 A | 8/1987 | Homonoff et al. |
| 4,693,056 A | 9/1987 | Raszewski |
| 4,701,239 A | 10/1987 | Craig |
| 4,720,415 A | 1/1988 | Vander Wielen et al. |
| 4,723,698 A | 2/1988 | Schoonderbeek |
| 4,726,874 A | 2/1988 | Van Vliet |
| 4,726,876 A | 2/1988 | Tomsovic, Jr. |
| 4,743,241 A | 5/1988 | Igaue et al. |
| 4,751,997 A | 6/1988 | Hirsch |
| 4,753,429 A | 6/1988 | Irvine et al. |
| 4,756,141 A | 7/1988 | Hirsch et al. |
| 4,763,822 A * | 8/1988 | Mohrsen ........................ 226/91 |
| 4,764,325 A | 8/1988 | Angstadt |
| 4,765,780 A | 8/1988 | Angstadt |
| 4,776,920 A | 10/1988 | Ryan |
| 4,777,513 A | 10/1988 | Nelson |
| 4,782,647 A | 11/1988 | Williams et al. |
| 4,785,986 A | 11/1988 | Daane et al. |
| 4,795,451 A | 1/1989 | Buckley |
| 4,795,510 A | 1/1989 | Wittrock et al. |
| 4,798,353 A | 1/1989 | Peugh |
| 4,801,345 A | 1/1989 | Dussaud et al. |
| 4,802,570 A | 2/1989 | Hirsch et al. |
| 4,840,609 A | 6/1989 | Jones et al. |
| 4,845,964 A | 7/1989 | Bors et al. |
| 4,864,802 A | 9/1989 | D'Angelo |
| 4,880,102 A | 11/1989 | Indrebo |
| 4,888,231 A | 12/1989 | Angstadt |
| 4,892,536 A | 1/1990 | Des Marais et al. |
| 4,904,440 A | 2/1990 | Angstadt |
| 4,908,175 A | 3/1990 | Angstadt |
| 4,909,019 A | 3/1990 | Delacretaz et al. |
| 4,915,767 A | 4/1990 | Rajala et al. |
| 4,917,746 A | 4/1990 | Kons |
| 4,925,520 A | 5/1990 | Beaudoin et al. |
| 4,927,322 A | 5/1990 | Schweizer et al. |
| 4,927,486 A | 5/1990 | Fattal et al. |
| 4,927,582 A | 5/1990 | Bryson |
| 4,937,887 A | 7/1990 | Schreiner |
| 4,963,072 A | 10/1990 | Miley et al. |
| 4,987,940 A | 1/1991 | Straub et al. |
| 4,994,010 A | 2/1991 | Doderer-Winkler |
| 5,000,806 A | 3/1991 | Merkatoris et al. |
| 5,021,111 A | 6/1991 | Swenson |
| 5,025,910 A | 6/1991 | Lasure et al. |
| 5,045,039 A | 9/1991 | Bay |
| 5,062,597 A | 11/1991 | Martin et al. |
| 5,064,179 A | 11/1991 | Martin |
| 5,064,492 A | 11/1991 | Friesch |
| 5,080,741 A | 1/1992 | Nomura et al. |
| 5,094,658 A | 3/1992 | Smithe et al. |
| 5,096,532 A | 3/1992 | Neuwirth et al. |
| 5,108,017 A | 4/1992 | Adamski, Jr. et al. |
| 5,109,767 A | 5/1992 | Nyfeler et al. |
| 5,110,403 A | 5/1992 | Ehlert |
| 5,127,981 A | 7/1992 | Straub et al. |
| 5,131,525 A | 7/1992 | Musschoot |
| 5,131,901 A | 7/1992 | Moll |
| 5,133,511 A | 7/1992 | Mack |
| 5,147,487 A | 9/1992 | Nomura et al. |
| 5,163,594 A | 11/1992 | Meyer |
| 5,171,239 A | 12/1992 | Igaue et al. |
| 5,176,244 A | 1/1993 | Radzins et al. |
| 5,183,252 A | 2/1993 | Wolber et al. |
| 5,188,627 A | 2/1993 | Igaue et al. |
| 5,190,234 A | 3/1993 | Ezekiel |
| 5,195,684 A | 3/1993 | Radzins |
| 5,203,043 A | 4/1993 | Riedel |
| 5,213,645 A | 5/1993 | Nomura et al. |
| 5,222,422 A | 6/1993 | Benner, Jr. et al. |
| 5,223,069 A | 6/1993 | Tokuno et al. |
| 5,226,992 A | 7/1993 | Morman |
| 5,246,433 A | 9/1993 | Hasse et al. |
| 5,252,228 A | 10/1993 | Stokes |
| 5,267,933 A | 12/1993 | Precoma |
| 5,273,228 A | 12/1993 | Yoshida |
| 5,275,676 A | 1/1994 | Rooyakkers et al. |
| 5,308,345 A | 5/1994 | Herrin |
| 5,328,438 A | 7/1994 | Crowley |
| 5,340,424 A | 8/1994 | Matsushita |
| 5,368,893 A | 11/1994 | Sommer et al. |
| 5,389,173 A | 2/1995 | Merkatoris et al. |
| 5,393,360 A | 2/1995 | Bridges et al. |
| 5,407,507 A | 4/1995 | Ball |
| 5,407,513 A | 4/1995 | Hayden et al. |
| 5,415,649 A | 5/1995 | Watanabe et al. |
| 5,421,924 A | 6/1995 | Ziegelhoffer et al. |
| 5,424,025 A | 6/1995 | Hanschen et al. |
| 5,429,576 A | 7/1995 | Doderer-Winkler |
| 5,435,802 A | 7/1995 | Kober |
| 5,443,437 A | 8/1995 | Mack |
| 5,449,353 A | 9/1995 | Watanabe et al. |
| 5,464,401 A | 11/1995 | Hasse et al. |
| 5,486,253 A | 1/1996 | Otruba |
| 5,494,622 A | 2/1996 | Heath et al. |
| 5,500,075 A | 3/1996 | Herrmann |
| 5,516,392 A | 5/1996 | Bridges et al. |
| 5,518,566 A | 5/1996 | Bridges et al. |
| 5,525,175 A | 6/1996 | Blenke et al. |
| 5,531,850 A | 7/1996 | Herrmann |
| 5,540,647 A | 7/1996 | Weiermann et al. |
| 5,545,275 A | 8/1996 | Herrin et al. |
| 5,545,285 A | 8/1996 | Johnson |
| 5,552,013 A | 9/1996 | Ehlert et al. |
| 5,556,360 A | 9/1996 | Kober et al. |
| 5,556,504 A | 9/1996 | Rajala et al. |
| 5,560,793 A | 10/1996 | Ruscher et al. |
| 5,575,187 A | 11/1996 | Dieterlen |
| 5,586,964 A | 12/1996 | Chase |

(56) References Cited

U.S. PATENT DOCUMENTS

| | | |
|---|---|---|
| 5,602,747 A | 2/1997 | Rajala |
| 5,603,794 A | 2/1997 | Thomas |
| 5,616,113 A | 4/1997 | Van Den Bergh |
| 5,624,420 A | 4/1997 | Bridges et al. |
| 5,624,428 A | 4/1997 | Sauer |
| 5,628,738 A | 5/1997 | Suekane |
| 5,634,917 A | 6/1997 | Fujioka et al. |
| 5,643,165 A | 7/1997 | Klekamp |
| 5,643,396 A | 7/1997 | Rajala et al. |
| 5,645,543 A | 7/1997 | Nomura et al. |
| 5,659,229 A | 8/1997 | Rajala |
| 5,660,657 A | 8/1997 | Rajala et al. |
| 5,660,665 A | 8/1997 | Jalonen |
| 5,683,376 A | 11/1997 | Kato et al. |
| 5,683,531 A | 11/1997 | Roessler et al. |
| RE35,687 E | 12/1997 | Igaue et al. |
| 5,693,165 A | 12/1997 | Schmitz |
| 5,699,653 A | 12/1997 | Hartman et al. |
| 5,705,013 A | 1/1998 | Nease |
| 5,707,470 A | 1/1998 | Rajala et al. |
| 5,711,832 A | 1/1998 | Glaug et al. |
| 5,725,518 A | 3/1998 | Coates |
| 5,725,714 A | 3/1998 | Fujioka |
| 5,743,994 A | 4/1998 | Roessler et al. |
| 5,745,922 A | 5/1998 | Rajala et al. |
| 5,746,869 A | 5/1998 | Hayden et al. |
| 5,749,989 A | 5/1998 | Linman et al. |
| 5,766,389 A | 6/1998 | Brandon et al. |
| 5,788,797 A | 8/1998 | Herrin et al. |
| 5,817,199 A | 10/1998 | Brennecke et al. |
| 5,829,164 A | 11/1998 | Kotitschke |
| 5,836,931 A | 11/1998 | Toyoda et al. |
| 5,858,012 A | 1/1999 | Yamaki et al. |
| 5,865,393 A | 2/1999 | Kreft et al. |
| 5,868,727 A | 2/1999 | Barr et al. |
| 5,876,027 A | 3/1999 | Fukui et al. |
| 5,876,792 A | 3/1999 | Caldwell |
| 5,879,500 A | 3/1999 | Herrin et al. |
| 5,902,431 A | 5/1999 | Wilkinson et al. |
| 5,932,039 A | 8/1999 | Popp et al. |
| 5,938,193 A | 8/1999 | Bluemle et al. |
| 5,964,390 A | 10/1999 | Boerresen et al. |
| 5,964,970 A | 10/1999 | Woolwine et al. |
| 6,022,443 A | 2/2000 | Rajala et al. |
| 6,036,805 A | 3/2000 | McNichols |
| 6,043,836 A | 3/2000 | Kerr et al. |
| 6,050,517 A | 4/2000 | Dobrescu et al. |
| 6,074,110 A | 6/2000 | Verlinden et al. |
| 6,076,442 A | 6/2000 | Arterburn et al. |
| 6,098,249 A | 8/2000 | Toney et al. |
| 6,123,792 A | 9/2000 | Samida et al. |
| 6,171,432 B1 | 1/2001 | Brisebois |
| 6,183,576 B1 | 2/2001 | Couillard et al. |
| 6,195,850 B1 | 3/2001 | Melbye |
| 6,210,386 B1 | 4/2001 | Inoue |
| 6,212,859 B1 | 4/2001 | Bielik, Jr. et al. |
| 6,214,147 B1 | 4/2001 | Mortellite et al. |
| 6,250,048 B1 | 6/2001 | Linkiewicz |
| 6,264,784 B1 | 7/2001 | Menard et al. |
| 6,276,421 B1 | 8/2001 | Valenti et al. |
| 6,276,586 B1 * | 8/2001 | Yeo et al. .................... 226/17 |
| 6,276,587 B1 | 8/2001 | Boerresen |
| 6,284,081 B1 | 9/2001 | Vogt et al. |
| 6,287,409 B1 | 9/2001 | Stephany |
| 6,306,122 B1 | 10/2001 | Narawa et al. |
| 6,309,336 B1 | 10/2001 | Muessig et al. |
| 6,312,420 B1 | 11/2001 | Sasaki et al. |
| 6,314,333 B1 | 11/2001 | Rajala et al. |
| 6,315,022 B1 | 11/2001 | Herrin et al. |
| 6,319,347 B1 | 11/2001 | Rajala |
| 6,336,921 B1 | 1/2002 | Kato et al. |
| 6,358,350 B1 | 3/2002 | Glaug et al. |
| 6,369,291 B1 | 4/2002 | Uchimoto et al. |
| 6,375,769 B1 | 4/2002 | Quereshi et al. |
| 6,391,013 B1 | 5/2002 | Suzuki et al. |
| 6,416,697 B1 | 7/2002 | Venturino et al. |
| 6,431,038 B2 | 8/2002 | Couturier |
| 6,440,246 B1 | 8/2002 | Vogt et al. |
| 6,443,389 B1 | 9/2002 | Palone |
| 6,446,795 B1 | 9/2002 | Allen et al. |
| 6,473,669 B2 | 10/2002 | Rajala et al. |
| 6,475,325 B1 | 11/2002 | Parrish et al. |
| 6,478,786 B1 | 11/2002 | Glaug et al. |
| 6,482,278 B1 | 11/2002 | McCabe et al. |
| 6,494,244 B2 | 12/2002 | Parrish et al. |
| 6,514,233 B1 | 2/2003 | Glaug |
| 6,521,320 B2 | 2/2003 | McCabe et al. |
| 6,523,595 B1 | 2/2003 | Milner et al. |
| 6,524,423 B1 | 2/2003 | Hilt et al. |
| 6,533,879 B2 | 3/2003 | Quereshi et al. |
| 6,540,857 B1 | 4/2003 | Coenen et al. |
| 6,547,909 B1 | 4/2003 | Butterworth |
| 6,551,228 B1 | 4/2003 | Richards |
| 6,551,430 B1 | 4/2003 | Glaug et al. |
| 6,554,815 B1 | 4/2003 | Umebayashi |
| 6,569,275 B1 | 5/2003 | Popp et al. |
| 6,572,520 B2 | 6/2003 | Blumle |
| 6,581,517 B1 | 6/2003 | Becker et al. |
| 6,585,841 B1 | 7/2003 | Popp et al. |
| 6,589,149 B1 | 7/2003 | VanEperen et al. |
| 6,596,107 B2 | 7/2003 | Stopher |
| 6,596,108 B2 | 7/2003 | McCabe |
| 6,605,172 B1 | 8/2003 | Anderson et al. |
| 6,605,173 B2 | 8/2003 | Glaug et al. |
| 6,637,583 B1 | 10/2003 | Anderson |
| 6,648,122 B1 | 11/2003 | Hirsch et al. |
| 6,649,010 B2 | 11/2003 | Parrish et al. |
| 6,651,923 B2 * | 11/2003 | Kinnunen et al. .......... 242/532.2 |
| 6,656,309 B1 | 12/2003 | Parker et al. |
| 6,659,150 B1 | 12/2003 | Perkins et al. |
| 6,659,991 B2 | 12/2003 | Suekane |
| 6,675,552 B2 | 1/2004 | Kunz et al. |
| 6,684,925 B2 | 2/2004 | Nagate et al. |
| 6,722,494 B2 | 4/2004 | Nakakado |
| 6,730,189 B1 | 5/2004 | Franzmann |
| 6,743,324 B2 | 6/2004 | Hargett et al. |
| 6,750,466 B2 | 6/2004 | Guha et al. |
| 6,758,109 B2 | 7/2004 | Nakakado |
| 6,766,817 B2 | 7/2004 | da Silva |
| 6,808,582 B2 | 10/2004 | Popp et al. |
| D497,991 S | 11/2004 | Otsubo et al. |
| 6,814,217 B2 | 11/2004 | Blumenthal et al. |
| 6,820,671 B2 | 11/2004 | Calvert |
| 6,837,840 B2 | 1/2005 | Yonekawa et al. |
| 6,840,616 B2 | 1/2005 | Summers |
| 6,852,186 B1 | 2/2005 | Matsuda et al. |
| 6,875,202 B2 | 4/2005 | Kumasaka et al. |
| 6,893,528 B2 | 5/2005 | Middelstadt et al. |
| 6,913,718 B2 | 7/2005 | Ducker |
| 6,918,404 B2 | 7/2005 | Dias da Silva |
| 6,942,759 B2 * | 9/2005 | Mohrsen et al. .............. 162/193 |
| 6,946,059 B2 * | 9/2005 | Mohrsen et al. .............. 162/255 |
| 6,976,521 B2 | 12/2005 | Mlinar |
| 6,978,486 B2 | 12/2005 | Zhou et al. |
| 7,017,820 B1 | 3/2006 | Brunner |
| 7,045,031 B2 | 5/2006 | Popp et al. |
| 7,066,586 B2 | 6/2006 | da Silva |
| 7,077,393 B2 | 7/2006 | Ishida |
| 7,130,710 B2 | 10/2006 | Popp et al. |
| 7,144,356 B2 | 12/2006 | Harnish |
| 7,172,666 B2 | 2/2007 | Groves et al. |
| 7,195,684 B2 | 3/2007 | Satoh |
| 7,201,345 B2 | 4/2007 | Werner |
| 7,214,174 B2 | 5/2007 | Allen et al. |
| 7,214,287 B2 | 5/2007 | Shiomi |
| 7,247,219 B2 | 7/2007 | O'Dowd |
| 7,303,708 B2 | 12/2007 | Andrews et al. |
| 7,380,213 B2 | 5/2008 | Pokorny et al. |
| 7,398,870 B2 | 7/2008 | McCabe |
| 7,449,084 B2 | 11/2008 | Nakakado |
| 7,452,436 B2 | 11/2008 | Andrews |
| 7,533,709 B2 | 5/2009 | Meyer |
| 7,537,215 B2 | 5/2009 | Beaudoin et al. |
| 7,587,966 B2 | 9/2009 | Nakakado et al. |

(56) References Cited

U.S. PATENT DOCUMENTS

| | | |
|---|---|---|
| 7,618,513 B2 | 11/2009 | Meyer |
| 7,638,014 B2 | 12/2009 | Coose et al. |
| 7,640,962 B2 | 1/2010 | Meyer et al. |
| 7,703,599 B2 | 4/2010 | Meyer |
| 7,708,849 B2 | 5/2010 | McCabe |
| 7,770,712 B2 | 8/2010 | McCabe |
| 7,771,407 B2 | 8/2010 | Umebayashi |
| 7,780,052 B2 | 8/2010 | McCabe |
| 7,809,179 B2 | 10/2010 | Singh et al. |
| 7,811,403 B2 | 10/2010 | Andrews |
| 7,861,756 B2 | 1/2011 | Jenquin et al. |
| 7,871,400 B2 | 1/2011 | Sablone et al. |
| 7,909,956 B2 | 3/2011 | Coose et al. |
| 7,975,584 B2 | 7/2011 | McCabe |
| 7,987,964 B2 | 8/2011 | McCabe |
| 8,007,484 B2 | 8/2011 | McCabe et al. |
| 8,007,623 B2 | 8/2011 | Andrews |
| 8,011,493 B2 | 9/2011 | Giuliani et al. |
| 8,016,972 B2 | 9/2011 | Andrews et al. |
| 8,257,535 B2 | 9/2012 | Yamamoto |
| 2001/0012813 A1 | 8/2001 | Bluemle |
| 2001/0017181 A1 | 8/2001 | Otruba et al. |
| 2002/0046802 A1 | 4/2002 | Tachibana et al. |
| 2002/0059013 A1 | 5/2002 | Rajala et al. |
| 2002/0096241 A1 | 7/2002 | Instance |
| 2002/0125105 A1 | 9/2002 | Nakakado |
| 2002/0162776 A1 | 11/2002 | Hergeth |
| 2003/0000620 A1 | 1/2003 | Herrin et al. |
| 2003/0015209 A1 | 1/2003 | Gingras et al. |
| 2003/0051802 A1 | 3/2003 | Hargett et al. |
| 2003/0052148 A1 | 3/2003 | Rajala et al. |
| 2003/0066585 A1 | 4/2003 | McCabe |
| 2003/0083638 A1 | 5/2003 | Molee |
| 2003/0084984 A1 | 5/2003 | Glaug et al. |
| 2003/0089447 A1 | 5/2003 | Molee et al. |
| 2003/0121614 A1 | 7/2003 | Tabor et al. |
| 2003/0135189 A1 | 7/2003 | Umebayashi |
| 2004/0007328 A1 | 1/2004 | Popp et al. |
| 2004/0016500 A1 | 1/2004 | Tachibana et al. |
| 2004/0044325 A1 | 3/2004 | Corneliusson |
| 2004/0087425 A1 | 5/2004 | Ng et al. |
| 2004/0112517 A1 | 6/2004 | Groves et al. |
| 2004/0164482 A1 | 8/2004 | Edinger |
| 2004/0182497 A1 | 9/2004 | Lowrey |
| 2005/0000628 A1 | 1/2005 | Norrby |
| 2005/0022476 A1 | 2/2005 | Hamer |
| 2005/0077418 A1 | 4/2005 | Werner et al. |
| 2005/0139713 A1 | 6/2005 | Weber et al. |
| 2005/0196538 A1 | 9/2005 | Sommer et al. |
| 2005/0230056 A1 | 10/2005 | Meyer et al. |
| 2005/0230449 A1 | 10/2005 | Meyer et al. |
| 2005/0233881 A1 | 10/2005 | Meyer |
| 2005/0234412 A1 | 10/2005 | Andrews et al. |
| 2005/0257881 A1 | 11/2005 | Coose et al. |
| 2005/0275148 A1 | 12/2005 | Beaudoin et al. |
| 2006/0021300 A1 | 2/2006 | Tada et al. |
| 2006/0137298 A1 | 6/2006 | Oshita et al. |
| 2006/0224137 A1 | 10/2006 | McCabe et al. |
| 2006/0265867 A1 | 11/2006 | Schaap |
| 2007/0045461 A1* | 3/2007 | Sartain et al. ............... 242/527 |
| 2007/0074953 A1 | 4/2007 | McCabe |
| 2008/0223537 A1 | 9/2008 | Wiedmann |
| 2009/0020211 A1 | 1/2009 | Andrews et al. |
| 2010/0078119 A1 | 4/2010 | Yamamoto |
| 2010/0078120 A1 | 4/2010 | Otsubo |
| 2010/0078127 A1 | 4/2010 | Yamamoto |
| 2010/0193138 A1 | 8/2010 | Eckstein |
| 2010/0193155 A1 | 8/2010 | Nakatani |

FOREIGN PATENT DOCUMENTS

| | | |
|---|---|---|
| CA | 1153345 | 9/1983 |
| CA | 1190078 | 7/1985 |
| CA | 1210744 | 9/1986 |
| CA | 1212132 | 9/1986 |
| CA | 1236056 | 5/1988 |
| CA | 1249102 | 1/1989 |
| CA | 1292201 | 11/1991 |
| CA | 1307244 | 9/1992 |
| CA | 1308015 | 9/1992 |
| CA | 1310342 | 11/1992 |
| CA | 2023816 | 3/1994 |
| CA | 2404154 | 10/2001 |
| CA | 2541194 | 10/2006 |
| CA | 2559517 | 4/2007 |
| CA | 2337700 | 8/2008 |
| CA | 2407867 | 6/2010 |
| DE | 60123502 | 10/2006 |
| DE | 60216550 | 12/2006 |
| DE | 102005048868 | 4/2007 |
| DE | 102006047280 | 4/2007 |
| EP | 0044206 | 1/1982 |
| EP | 0048011 | 3/1982 |
| EP | 0089106 | 9/1983 |
| EP | 0099732 | 2/1984 |
| EP | 0206208 | 12/1986 |
| EP | 0304140 | 2/1989 |
| EP | 0439897 | 8/1991 |
| EP | 0455231 A1 | 11/1991 |
| EP | 510251 | 10/1992 |
| EP | 0652175 A1 | 5/1995 |
| EP | 0811473 | 12/1997 |
| EP | 0901780 | 3/1999 |
| EP | 0990588 | 4/2000 |
| EP | 1132325 A2 | 9/2001 |
| EP | 1199057 | 4/2002 |
| EP | 1272347 A0 | 1/2003 |
| EP | 1366734 | 12/2003 |
| EP | 1504738 A2 | 2/2005 |
| EP | 1571249 | 9/2005 |
| EP | 1619008 | 1/2006 |
| EP | 1707168 A2 | 10/2006 |
| EP | 1726414 | 11/2006 |
| EP | 1302424 | 12/2006 |
| EP | 1801045 | 6/2007 |
| EP | 1941853 | 7/2008 |
| EP | 2233116 | 9/2010 |
| EP | 2238955 | 10/2010 |
| ES | 509706 | 11/1982 |
| ES | 520559 | 12/1983 |
| ES | 296211 | 12/1987 |
| ES | 200601373 | 7/2009 |
| ES | 2311349 | 9/2009 |
| FR | 2177355 | 11/1973 |
| FR | 2255961 | 7/1975 |
| FR | 1132325 | 10/2006 |
| FR | 2891811 | 4/2007 |
| GB | 191101501 A | 0/1912 |
| GB | 439897 | 12/1935 |
| GB | 856389 | 12/1960 |
| GB | 941073 | 11/1963 |
| GB | 1096373 | 12/1967 |
| GB | 1126539 | 9/1968 |
| GB | 1346329 | 2/1974 |
| GB | 1412812 | 11/1975 |
| GB | 2045298 | 10/1980 |
| GB | 2115775 | 9/1983 |
| GB | 2288316 | 10/1995 |
| IT | 1374910 | 5/2010 |
| IT | 1374911 | 5/2010 |
| JP | 428364 | 1/1992 |
| JP | 542180 | 2/1993 |
| JP | 576566 | 3/1993 |
| JP | 626160 | 2/1994 |
| JP | 626161 | 2/1994 |
| JP | 6197925 A | 7/1994 |
| JP | 9299398 | 11/1997 |
| JP | 10035621 | 2/1998 |
| JP | 10-277091 A | 10/1998 |
| SE | 0602047 | 5/2007 |
| SE | 0601003-7 | 6/2007 |
| SE | 0601145-6 | 10/2009 |
| WO | WO2008155618 | 12/1988 |

(56) References Cited

FOREIGN PATENT DOCUMENTS

| | | |
|---|---|---|
| WO | WO9403301 | 2/1994 |
| WO | WO9732552 | 9/1997 |
| WO | WO9747265 | 12/1997 |
| WO | WO9747810 | 12/1997 |
| WO | WO9821134 | 5/1998 |
| WO | WO9907319 | 2/1999 |
| WO | WO9913813 A1 | 3/1999 |
| WO | WO9932385 | 7/1999 |
| WO | WO9965437 | 12/1999 |
| WO | WO0143682 | 6/2001 |
| WO | WO0172237 A2 | 10/2001 |
| WO | WO2004007329 | 1/2004 |
| WO | WO2005075163 | 8/2005 |
| WO | WO2007029115 | 3/2007 |
| WO | WO2007039800 | 4/2007 |
| WO | WO2007126347 | 11/2007 |
| WO | WO2008001209 | 1/2008 |

OTHER PUBLICATIONS

USPTO Office Action regarding U.S. Appl. No. 11/880,261, dated Jul. 23, 2009, 14 pages.

USPTO Office Action regarding U.S. Appl. No. 11/880,261, dated Mar. 10, 2010, 11 pages.

USPTO Office Action regarding U.S. Appl. No. 11/880,261, dated Nov. 9, 2010, 14 pages.

USPTO Office Action regarding U.S. Appl. No. 11/880,261, dated Jun. 23, 2011, 10 pages.

"Reciprocating Mechanisms", Franklin Jones, vol. 1, date unknown, 2 pp.

European Search Report regarding Application No. EP11250709, dated Oct. 17, 2014, 9 pages.

* cited by examiner

APPARATUS AND METHOD FOR MINIMIZING WASTE AND IMPROVING QUALITY AND PRODUCTION IN WEB PROCESSING OPERATIONS BY AUTOMATED THREADING AND RE-THREADING OF WEB MATERIALS

RELATED APPLICATIONS

This application claims the benefit of U.S. provisional patent application Ser. No. 61/400,318 filed 26 Jul. 2010. This application is also a continuation-in-part of co-pending U.S. patent application Ser. No. 11/880,261, filed on Jul. 20, 2007.

BACKGROUND OF THE INVENTION

The invention disclosed herein relates to apparatus and methods for waste reduction and improvements to the quality and production in web processing operations, such as diaper manufacturing. While the description provided relates to diaper manufacturing, the apparatus and method are easily adaptable to other applications.

Generally, diapers comprise an absorbent insert or patch and a chassis, which, when the diaper is worn, supports the insert proximate a wearer's body. Additionally, diapers may include other various patches, such as tape tab patches, reusable fasteners and the like. The raw materials used in forming a representative insert are typically cellulose pulp, tissue paper, poly, nonwoven web, acquisition, and elastic, although application specific materials are sometimes utilized. Usually, most of the insert raw materials are provided in roll form, and unwound and applied in assembly line fashion.

In the creation of a diaper, multiple roll-fed web processes are typically utilized. To create an absorbent insert, the cellulose pulp is unwound from the provided raw material roll and pulverized by a pulp mill. Discrete pulp cores are formed by a core forming assembly and placed on a continuous tissue web. Optionally, super-absorbent powder may be added to the pulp core. The tissue web is wrapped around the pulp core. The wrapped core is debulked by proceeding through a calender unit, which at least partially compresses the core, thereby increasing its density and structural integrity. After debulking, the tissue-wrapped core is passed through a segregation or knife unit, where individual wrapped cores are cut. The cut cores are conveyed, at the proper pitch, or spacing, to a boundary compression unit.

While the insert cores are being formed, other insert components are being prepared to be presented to the boundary compression unit. For instance, the poly sheet is prepared to receive a cut core. Like the cellulose pulp, poly sheet material is usually provided in roll form. The poly sheet is fed through a splicer and accumulator, coated with an adhesive in a predetermined pattern, and then presented to the boundary compression unit. In addition to the poly sheet, which may form the bottom of the insert, a two-ply top sheet may also be formed in parallel to the core formation. Representative plies are an acquisition web material and a nonwoven web material, both of which are fed from material rolls, through a splicer and accumulator. The plies are coated with adhesive, adhered together, cut to size, and presented to the boundary compression unit. Therefore, at the boundary compression unit, three components are provided for assembly: the poly bottom sheet, the core, and the two-ply top sheet.

A representative boundary compression unit includes a die roller and a platen roller. When all three insert components are provided to the boundary compression unit, the nip of the rollers properly compresses the boundary of the insert. Thus, provided at the output of the boundary compression unit is a string of interconnected diaper inserts. The diaper inserts are then separated by an insert knife assembly and properly oriented. At this point, the completed insert is ready for placement on a diaper chassis.

A representative diaper chassis comprises nonwoven web material and support structure. The diaper support structure is generally elastic and may include leg elastic, waistband elastic and belly band elastic. The support structure is usually sandwiched between layers of the nonwoven web material, which is fed from material rolls, through splicers and accumulators.

The present invention relates to disposable hygiene products and to methods and apparatuses for processing components of disposable hygiene products. More specifically, the invention relates to manufacturing a stretchable breathable laminate that is bonded at a plurality of bond sites.

Elastic laminates can be formed of a layer of stretched elastic between two non-stretched layers of non-woven material. Once the stretched elastic layer is bonded with the non-stretched non-woven, a stretch engine is formed once the elastic material is allowed to relax, forming a laminate that can be stretched in the machine direction.

During construction of such laminates, defects in the elastic material supplied to the process can result in snapped or otherwise unacceptable elastic introduced to the system. If such unacceptable elastic is introduced into the laminate, the manufacturing process can require slowing or stoppage in order for properly produced laminate to be re-introduced into the process. One aspect of the present invention relates to an automated method and apparatus to first detect such defects, and to automatically re-thread the elastic material through stretch rollers and continue with the processing sequence using acceptable elastic material resulting in an acceptable formed laminate.

Such automation results in less manual threading and re-threading, and less system downtime and scrapped product (resulting from unacceptable elastic forming unacceptable laminate).

The chassis may also be provided with several patches, besides the absorbent insert. Representative patches include adhesive tape tabs and resealable closures.

The process utilizes two main carrier webs; a nonwoven web which forms an inner liner web, and an outer web that forms an outwardly facing layer in the finished diaper. In a representative chassis process, the nonwoven web is slit at a slitter station by rotary knives along three lines, thereby forming four webs. One of the lines is on approximately the centerline of the web and the other two lines are parallel to and spaced a short distance from the centerline. The effect of such slicing is twofold; first, to separate the nonwoven web into two inner diaper liners. One liner will become the inside of the front of the diaper, and the second liner will become the inside of the back of that garment. Second, two separate, relatively narrow strips are formed that may be subsequently used to cover and entrap portions of the leg-hole elastics. The strips can be separated physically by an angularly disposed spreader roll and aligned laterally with their downstream target positions on the inner edges of the formed liners.

After the nonwoven web is sliced, an adhesive is applied to the liners in a predetermined pattern in preparation to receive leg-hole elastic. The leg-hole elastic is applied to the liners and then covered with the narrow strips previously separated from the nonwoven web. Adhesive is applied to the outer web, which is then combined with the assembled inner webs having elastic thereon, thereby forming the diaper chassis. Next, after the elastic members have been sandwiched between the inner and outer webs, an adhesive is applied to the chassis. The chassis is now ready to receive an insert.

To assemble the final diaper product, the insert must be combined with the chassis. The placement of the insert onto the chassis occurs on a placement drum or at a patch applicator. The inserts are provided to the chassis on the placement drum at a desired pitch or spacing. The generally flat chassis/insert combination is then folded so that the inner webs face each other, and the combination is trimmed. A sealer bonds the webs at appropriate locations prior to individual diapers being cut from the folded and sealed webs.

Roll-fed web processes typically use splicers and accumulators to assist in providing continuous webs during web processing operations. A first web is fed from a supply wheel (the expiring roll) into the manufacturing process. As the material from the expiring roll is depleted, it is necessary to splice the leading edge of a second web from a standby roll to the first web on the expiring roll in a manner that will not cause interruption of the web supply to a web consuming or utilizing device.

In a splicing system, a web accumulation dancer system may be employed, in which an accumulator collects a substantial length of the first web. By using an accumulator, the material being fed into the process can continue, yet the trailing end of the material can be stopped or slowed for a short time interval so that it can be spliced to leading edge of the new supply roll. The leading portion of the expiring roll remains supplied continuously to the web-utilizing device. The accumulator continues to feed the web utilization process while the expiring roll is stopped and the new web on a standby roll can be spliced to the end of the expiring roll.

In this manner, the device has a constant web supply being paid out from the accumulator, while the stopped web material in the accumulator can be spliced to the standby roll. Examples of web accumulators include that disclosed in U.S. patent application Ser. No. 11/110,616, which is commonly owned by the assignee of the present application, and incorporated herein by reference.

As in many manufacturing operations, waste minimization is a goal in web processing applications, as products having spliced raw materials cannot be sold to consumers. Indeed, due to the rate at which web processing machines run, even minimal waste can cause inefficiencies of scale. In present systems, waste materials are recycled. However, the act of harvesting recyclable materials from defective product is intensive. That is, recyclable materials are harvested only after an identification of a reject product at or near the end of a process. The result is that recyclable materials are commingled, and harvesting requires the extra step of separating waste components. Therefore, the art of web processing would benefit from systems and methods that identify potentially defective product prior to product assembly, thereby eliminating effort during recyclable material harvesting.

Furthermore, to improve quality and production levels by eliminating some potentially defective product, the art of web processing would benefit from systems and methods that ensure higher product yield and less machine downtime.

SUMMARY OF THE INVENTION

Provided are method and apparatus for minimizing waste and improving quality and production in web processing operations.

Importantly, the methods taught in the present application are applicable not only to diapers and the like, but in any web based operation. The waste minimization techniques taught herein can be directed any discrete component of a manufactured article, i.e., the methods taught herein are not product specific. For instance, the present methods can be applied as easily with respect to diaper components as they can for feminine hygiene products, as they can for face masks in which components such as rubber bands and nose pieces are used.

For instance, by practicing the methods of the present invention, waste of staples and elastic bands can be avoided during manufacture of face masks, for instance those disclosed in U.S. Pat. No. 7,131,442. One of the objectives is simply to recognize product during manufacture that ultimately would fail quality control inspection, and avoid placing material on to that product during the manufacturing processes.

As another example, the amount of adhesive applied to certain products can be reduced by not applying adhesive to products that have already been determined to be defected or assigned to rejection. For instance, in U.S. Pat. No. 6,521,320, adhesive application is shown for example in FIG. 11. By assigning or flagging product that has already been determined to end up in a scrap or recycling pile, the adhesive flow can be stopped or minimized.

In yet another exemplary application of the methods of the present invention, discrete components or raw material carried on products that have already been determined to be defected or assigned to rejection can also be removed and recycled prior to commingling with other discrete components or raw material. For instance, if an absorbent pad, such as shown at reference numeral 40 of U.S. Pat. No. 6,521,320 is destined for application to a product that has already been determined to be defected or assigned to rejection, the absorbent pad can be withdrawn from the product, or never introduced in the first instance. For example, during startup or shutdown of high speed diaper manufacturing operations, a certain number of products is routinely discarded into recycling. By identification of the start up or shut down routine, avoidance of introduction of absorbent pads can be achieved. Alternatively, during stand-by, the absorbent pads often degrade by accumulation of dust. By identifying which products would bear the dust, the absorbent pads can be withdrawn from further manufacture, and no additional components would be applied to such a product.

In one embodiment, a method for assembling a plurality of continuous webs is provided, including defining first web inspection parameters and inspecting at least one of the plurality of continuous webs to determine whether the at least one web conforms to the first web inspection parameters. Further, the method involves providing a chassis web which is adapted to receive a patch and providing a patch web from which the patch is cut. Finally, the cut patch is applied to the chassis web if the inspected web conforms to the first web inspection parameters. In another embodiment, the method also includes steps of defining first patch inspection parameters and inspecting a cut patch to determine whether the patch conforms to the first patch inspection parameters. While the patch inspection may provide interesting diagnostic information related to a web processing machine, the application of the patch may be limited to those patches that conform to the first patch inspection parameters.

Another embodiment of the method of the present invention involves defining first web inspection parameters and a product pitch. Generally in any web process, a web is provided, which is traveling at a web velocity. This embodiment involves inspecting the web to determine whether the web conforms to the first web inspection parameters and producing an inspection value as a result of the inspecting step. This value is then recorded once per sample time interval. The sample time interval may be calculated by dividing the defined product pitch by the web velocity. While the inspection value may be as simple as a bivalent value, a more informational multivalent value may be used.

In addition to the web process provided, an apparatus for carrying out the process is provided. An embodiment of the apparatus includes a continuous web supply providing continuous web material from an upstream position to a downstream position and a means for providing a patch spaced from a first side of the continuous web material. A patch applicator is provided to alter the space between the patch providing means and the continuous web material and a web inspection device is positioned upstream from the patch applicator. Additionally, a programmable controller receives an input from the web inspection device and provides an output to the patch applicator. The web processing apparatus may also include a patch inspection device that provides an output to the programmable controller. A patch reject conveyor may be positioned to receive defective patches from the patch providing means. In another embodiment of a web processing apparatus, a product inspection device may be located downstream from the patch applicator to provide an output to the programmable controller. Also, a product reject conveyor could be adapted to divert defective product as indicated by the product inspection device.

DESCRIPTION OF THE PREFERRED EMBODIMENT

Although the disclosure hereof is detailed and exact to enable those skilled in the art to practice the invention, the physical embodiments herein disclosed merely exemplify the invention which may be embodied in other specific structures. While the preferred embodiment has been described, the details may be changed without departing from the invention, which is defined by the claims.

It is noted that the present waste minimization techniques and apparatus are described herein with respect to products such as diapers, but as previously mentioned, can be applied to a wide variety of processes in which discrete components are applied sequentially.

Figure 1:
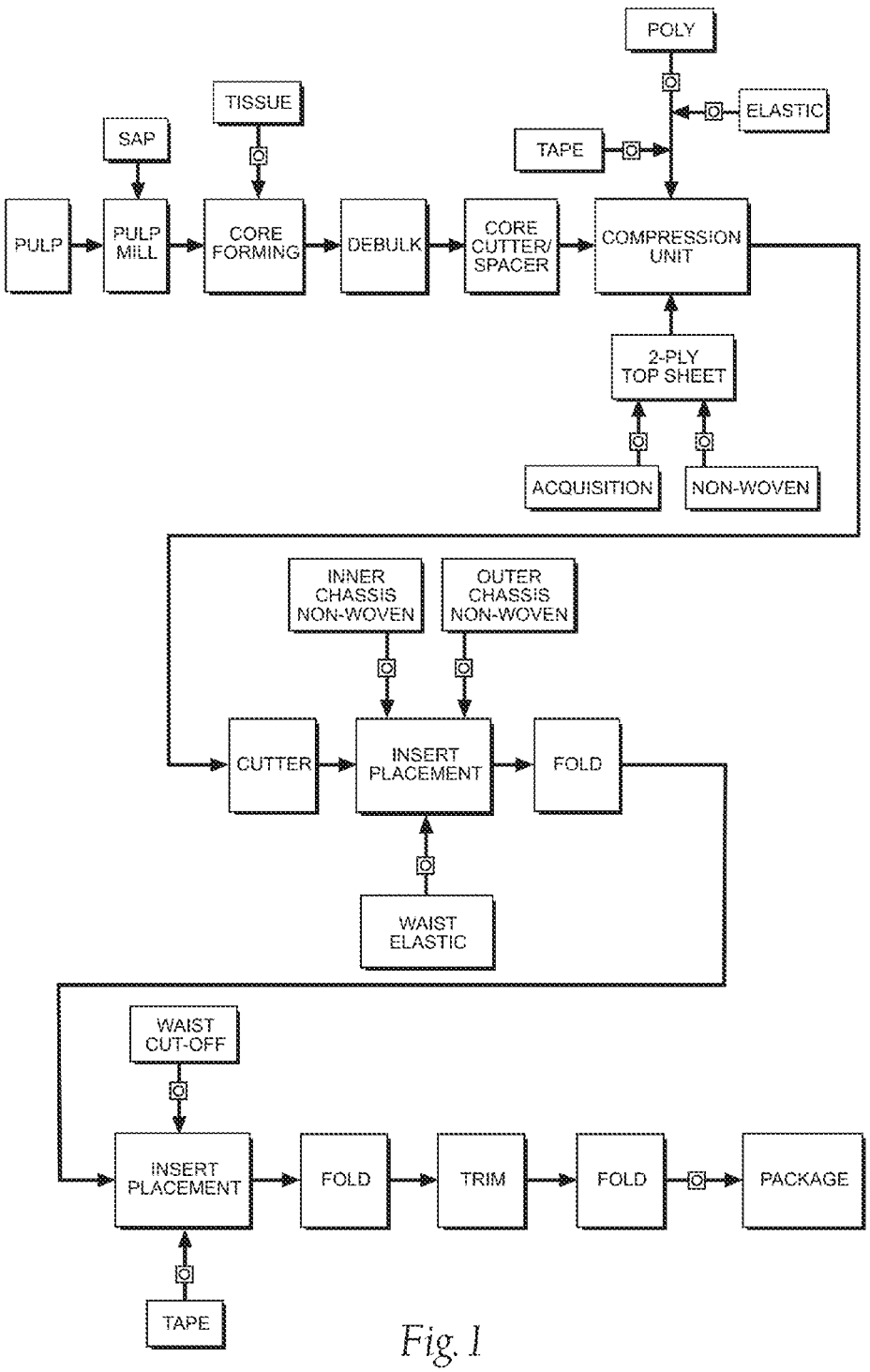
FIG. 1 is a schematic of a representative web processing system.

Referring to FIG. 1, a web processing operation starts with incorporating raw materials such as paper pulp and super absorbent polymer (SAP) in a pulp mill. The mixture is sent to a core forming drum, where cores are formed for retaining liquids. A core can be placed on a tissue and processed as shown. Eventually, an additional tissue layer is formed, sandwiching the core.

The process continues through debulking, core cutting and spacing, optionally, compression, and application of tape and elastics. The process then proceeds with application of outer and inner non-woven layers, and waist elastic. The web can undergo folding, extraction and trimming of excess material, and application of material to tighten the diaper about the waist. Eventually, the product is folded and packaged.

As seen on FIG. 1, the symbol is shown at locations of introductions of discrete components into the process. At these locations, inspection can take place to determine the presence or absence of acceptable product introduction. In addition to visual inspection, operational characteristics such as startup/ramp-up/shutdown operations can trigger waste minimization techniques as will be described later.

At each of these operations shown in FIG. 1, diagnostics can be performed to indicate whether the product meets acceptable criteria. If so, discrete elements, such as the core, tissue layers, elastic, etc., continue to be applied in a sequence such as shown in FIG. 1. If not, no additional discrete elements need be applied.

Figure 2A:
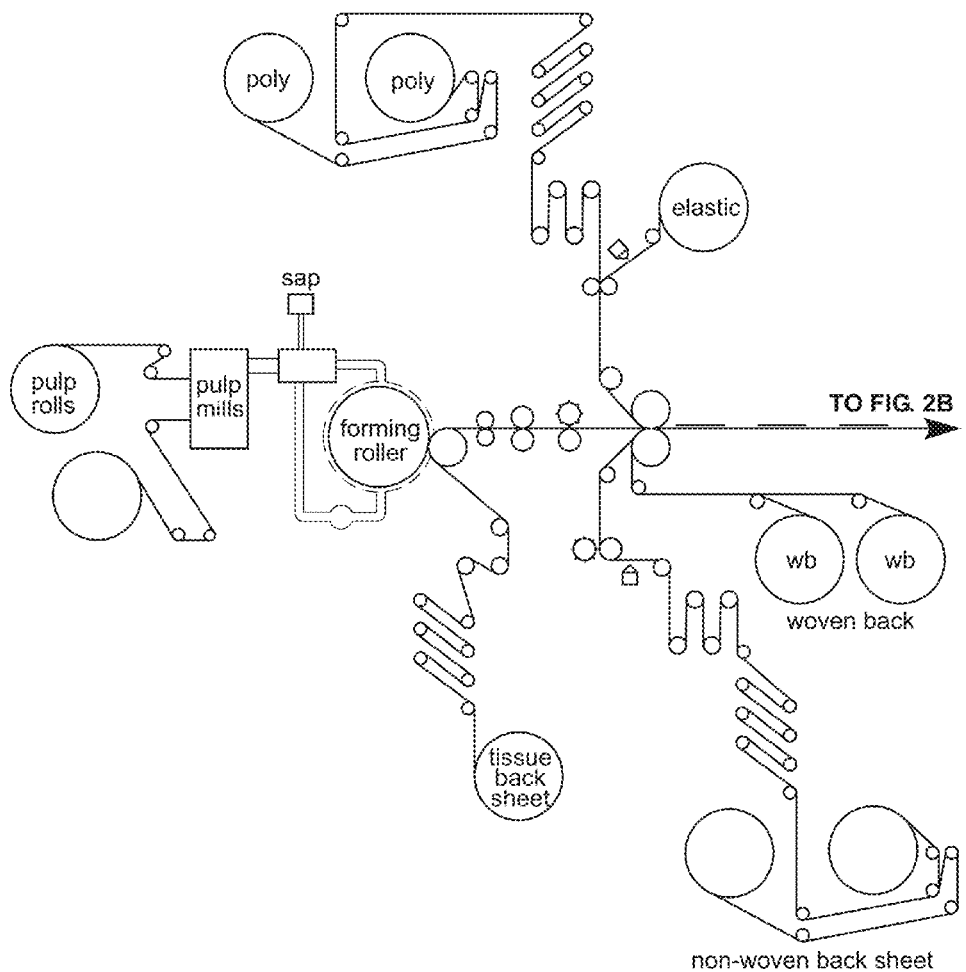
FIG. 2A-2C are schematic representations of a web processing system incorporating principles of the present invention.
Figure 2B:
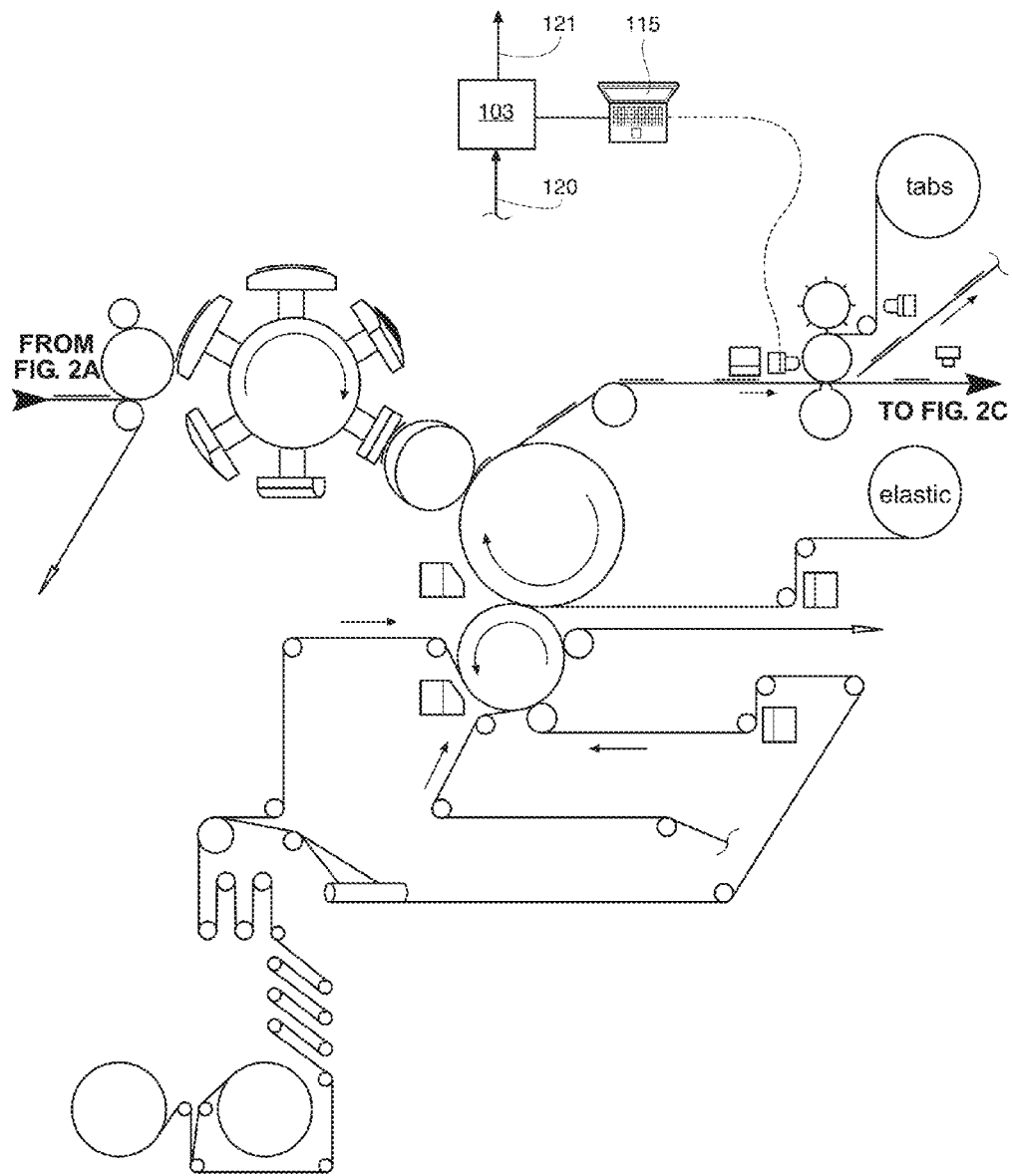
Figure 2C:
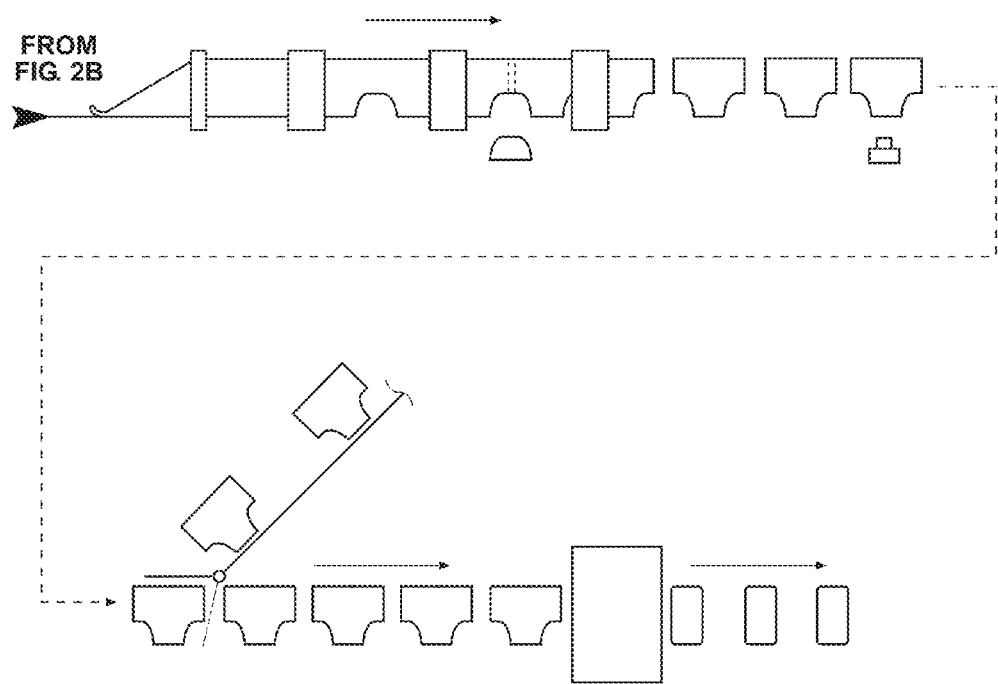

Referring now to FIGS. 2a-c, a web processing operation incorporating the present invention is shown.

Referring now to FIG. 2, an additional schematic of processes of the present invention is shown. As indicated, pulp rolls 200 feed raw pulp 201 into a pulp mill 204, where the pulp is pulverized. Super absorbent polymer is added from station 206. The SAP laced pulp is fed onto core forming roller 208. Cores 210 from core forming roller 208 are applied to the tissue back sheet 214 which has been introduced through tissue back sheet feeder 212. Following debulking station 216 and core cutting and spacing station 218, an infeed of poly layer 220, elastic layer 222 is applied to the carrier web, in addition to non woven layer 224 and two ply top sheet woven 226. This web then is cut at cutting station 228 into discrete inserts 230, which are then typically placed on a article transfer and placement apparatus with active puck 230. This device is disclosed in U.S. patent application Ser. No. 11/357,546, owned by the same assignee as the present case, and which is incorporated herein by reference.

The process utilizes two main carrier webs; a nonwoven web 11 which forms an inner liner web, and a web 12 that forms an outwardly facing layer in the finished diaper 50. In this embodiment, the nonwoven web 11 is slit, at slitter station 15, by rotary knives 14 along three lines. One of these lines is preferably on approximately the centerline of web 11 and the other two lines are parallel to and spaced a short distance from the centerline. The effect is twofold; first, to separate web 11 into two inner liners 20. One liner will become the inside of the front of the diaper 50 and the second liner will become the inside of the back of that garment. Second, two separate, relatively narrow strips 22 and 24 are formed which are subsequently used to cover and entrap portions of leg-hole elastics 26. Strips 22 and 24 are separated physically by an angularly disposed spreader roll 23 and aligned laterally with their downstream target positions on the inner edges of the liner webs 20.

Adhesive patterns are applied to the liner webs 20 in target areas for the leg-hole elastics 26. A spray gun assembly 29 of a type known in the art is preferably used to apply the adhesive patterns. Two sets of leg-hole, elastic strands 26 are introduced through laydown guides 30, which reciprocate from side to side past each other. The strands 26 are glued to the web sections 20, their laydown patterns following a serpentine path. Given the absence of adhesive in the area separating the inner liners 20, for some portion of each successive diaper product, the strands 26 each track parallel to the inner slit edges of the web sections 20. Laydown guides 30 then apply the strands 26, which form leg-hole elastics as the web sections 20 are carried along the face of a drum or roll 32. Those parts of the elastic patterns which are near the inner slit edges of webs 20 are then covered by the introduction of an adhesive lamination thereover of the strips 22 and 24 of nonwoven web also against the drum 32.

The side-to-side excursions of the leg-hole elastic laydown guides 30 result in arcuate segments of elastic strands extending on each side of the web centerline. After the nonwoven strips 22 and 24 have been applied to cover and entrap those parts of the elastics 26 that run nearest to and parallel to the inner edges of the webs 20, a second pair of slitter knives 34 is used to trim away a portion of the narrow nonwoven strips 22, 24, along with that part of the inner liner webs 20 to which they are laminated. This also removes those portions of the elastic strands 26 which are contained within the laminations. The resultant trimmed scrap strips 36 are removed from the process for disposal elsewhere.

The effect of the last-described step is to remove the cut away portions of the elastic, eliminating its corresponding unwanted gathering effect from the crotch region of the garments 50. The remaining portions of the curved elastic strands create a gathering effect around the leg openings of the finished garments 50.

Subsequent to the combining and trimming of the inner webs 20 and the cover strips 22, 24, the combining drum 32 carries the webs to a nip with a second combining drum 38, where the web sections 20, with their respective curved elastic patterns exposed, are transferred to and laminated adhesively against the inside face of outer liner web 12. This process entraps the curved elastic patterns 26 between the inner liners 20 and outer web 12 thereby forming a composite web 39.

The composite web 39 is then provided with a pattern of adhesive in preparation to receive an absorbent insert or patch 46. The patch 46 is cut from a provided patch web 40 by a cooperation of a cutter 41 and an anvil surface on a vacuum roll 42 and rotated into position for transfer to the composite web 39 by a patch applicator 105. If the patch 46 is to be applied to the web 39—a determination explained more fully below—the patch applicator 105 forces the web 39 against the patch 46, thereby adhering the patch 46 to the web 39.

Leg-hole materials 48, if not previously removed, are cut at a cutting station 47, thereby removing the material 48 contained within an approximate perimeter defined by the curved pattern of the elastics 26. The running composite chassis web 39 is folded, before or after cutting out of the leg holes, longitudinally along its centerline, thereby generally aligning its front waist edge with its back waist edge. The regions 53 which are to become the side seams 54 of the garments 50 are then welded by a sealing device 49 either ultrasonically or by heat. Note that the leg holes are preferably cut out before this point, leaving only a narrow zone for welding. The weld pattern is preferably wide enough to extend into both the left side seam of one garment and the right side seam of the adjacent garment. The garments 50 are then separated by passing through a cut-off knife assembly 55, which severs the web along the transverse axis of the side seam weld 53.

In addition to the exemplary components generally found in a web processing apparatus, the present device and methods further include an advanced defect detection system. An embodiment of the defect detection system preferably comprises at least one visual inspection station 101, but preferably a plurality of visual inspection stations 101. Each visual inspection station 101 may include a vision sensor, such as an In-Sight Vision Sensor available from Cognex Corporation of Natick, Mass. Since each component part of a product resulting from a web process has a point of incorporation into the product, visual inspection of each component part preferably occurs prior to the point of incorporation. The results of the visual inspections that occur are relayed from each visual inspection station 101 to a programmable logic controller (PLC) 103. Each visual inspection station 101 may provide diagnostic capability by monitoring lighting, focus and positioning.

Machine vision systems typically require digital input/output devices and computer networks to control other manufacturing equipment, in this case the splicing unit.

A typical machine vision system will consist of several among the following components:

One or more digital or analog camera (black-and-white or colour) with suitable optics for acquiring images
Lighting
Camera interface for digitizing images (widely known as a "frame grabber")
A processor (often a PC or embedded processor, such as a DSP)
Computer software to process images and detect relevant features.
A synchronizing sensor for part detection (often an optical or magnetic sensor) to trigger image acquisition and processing.
Input/Output hardware (e.g. digital I/O) or communication links (e.g. network connection or RS-232) to report results
Some form of actuators used to sort or reject defective parts.

The sync sensor determines when a part (often moving on a conveyor) is in position to be inspected. The sensor triggers the camera to take a picture of the part as it passes by the camera and often synchronizes a lighting pulse. The lighting used to illuminate the part is designed to highlight features of interest and obscure or minimize the appearance of features that are not of interest (such as shadows or reflections).

The camera's image can be captured by the framegrabber. A framegrabber is a digitizing device (within a smart camera or as a separate computer card) that converts the output of the camera to digital format (typically a two dimensional array of numbers, corresponding to the luminous intensity level of the corresponding point in the field of view, called pixel) and places the image in computer memory so that it may be processed by the machine vision software.

The software will typically take several steps to process an image. In this case, the image processing will result in either detection of the indicator material, or non-detection of the indicator material.

Commercial and open source machine vision software packages typically include a number of different image processing techniques such as the following:

Pixel Counting: counts the number of light or dark pixels

Thresholding: converts an image with gray tones to simply black and white

Segmentation: used to locate and/or count parts

Blob Discovery & Manipulation: inspecting an image for discrete blobs of connected pixels (e.g. a black hole in a grey object) as image landmarks. These blobs frequently represent optical targets for machining, robotic capture, or manufacturing failure.

Recognition-by-Components: extracting geons from visual input

Robust Pattern Recognition: location of an object that may be rotated, partially hidden by another object, or varying in size Barcode Reading: decoding of 1D and 2D codes designed to be read or scanned by machines Optical Character Recognition: automated reading of text such as serial numbers Gauging: measurement of object dimensions in inches or millimeters Edge Detection: finding object edges Template Matching: finding, matching, and/or counting specific patterns.

In most cases, a machine vision system will use a sequential combination of these processing techniques to perform a complete inspection. A system that reads a barcode may also check a surface for scratches or tampering and measure the length and width of a machined component.

Additionally, machine downtime can be minimized by the provision of systems and methods for warning a machine operator of expected machine troubles so that scheduled maintenance can occur.

The PLC 103 includes software adapted to run several routines that may be initiated by some triggering event, such as an automatic detection of a defined condition or manual input by a machine operator. Some routines are run during machine setup while other routines are run during machine operation, while still other routines are run during machine diagnostics at some point during machine downtime.

The PLC 103 generally receives inputs 120 from the visual inspection stations 101, from the various machine components, or from manual input by a machine operator on an operator interface, or human machine interface (HMI) 115. Some of the inputs can also be from stations near the pulp rolls, pulp mills, forming rollers, or elsewhere in the system where inspection is present.

The HMI 115 provides an interface for user interaction with the web processing machinery and may comprise a pressure sensitive touch screen, a keyboard, a computer mouse, or even a wireless device providing such an interface. The PLC 103 preferably provides controlling outputs 121 to the patch applicator 105, the cutter 41 and vacuum roll 42, a patch reject conveyor 107 and a product reject conveyor 109.

The input to the PLC 103 from each inspection station 101 preferably comprises a defect indicator 111 that represents a detected web defect at a position in the process a number of patch placements from the patch applicator 105. That is, at any given time during machine operation, between any inspection station 101 and any patch applicator 105 in a web process, there exists material sufficient to produce a determinable number of products having a patch applied thereto. Therefore, a defect may be detected and flagged as corresponding to a specific product location throughout the process.

In determining whether a patch should be applied to a product by a patch applicator 105, the PLC 103 stores a product status indicator for each product in the process, preferably for each product between the product reject conveyor 109 and most remote visual inspection station 101. The status indicator accumulates defect indicators 111 from the inspection stations 101 to track the progress of a product through the process.

A preferred product status indicator is a byte of digital data, with each bit reflecting the defect indicator 111 for the tagged product from an inspection station 101. For example, the least significant bit in the status indicator may represent the defect indicator for the most remote visual inspection station 101. As the bit significance increases, so does the proximity of the respective inspection station 101 to the product reject conveyor 109. A byte of data would provide for the possibility of eight inspection stations, and specific tracking of defects at those inspection stations. To store the product status indicator, the PLC 103 preferably includes some volatile and some nonvolatile computer memory. The volatile memory may provide quicker access times during machine operation, while the nonvolatile memory could be used to store product status indicators when the machine is paused. The minimum amount of memory required by the PLC 103 is at least partly determined by the number of visual inspection stations 101 and the number of potential products in queue between the first visual inspection station 101 and the product reject conveyor 109. For example, if a web process utilizes eight visual inspection stations 101 and two hundred products could be in queue in any given time, a volatile memory of at least two hundred bytes would be required.

The visual inspection station outputs may be sampled synchronously, or the outputs may be asynchronously analyzed by the PLC 103. If synchronous, the outputs may be sampled at a rate equal to the speed of the traveling webs divided by the product pitch, or product size. To enable use of different product sizes in a given process, the sample timing of the inspection station results may be varied, accordingly.

In addition to synchronous sampling of the inspection station results, the results could be analyzed asynchronously, which may be advantageous if various materials are incorporated into the process at different rates. Asynchronous analysis of the outputs, however, may provide less visibility into the specific defects included in a completed product.

Figure 3:
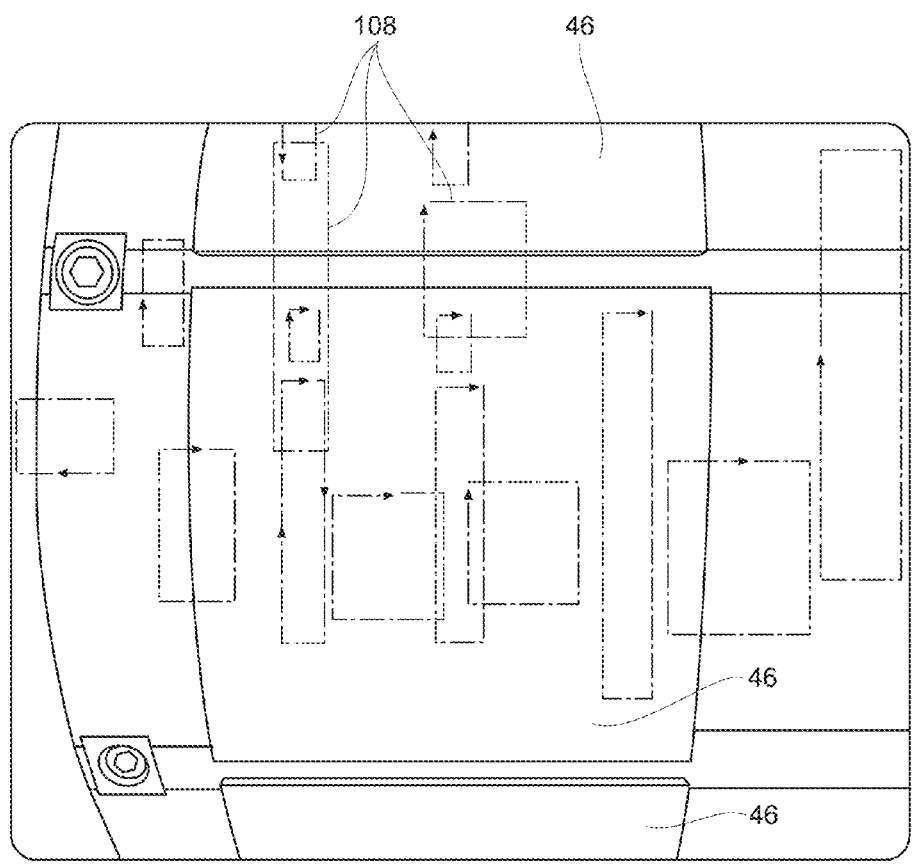
FIG. 3 is an elevation view of a patch inspection.

Prior to operating or running a web process, the machinery must be threaded with raw patch web material. The PLC 103 may provide a software routine, such as an automatic web threading routine, for aiding such setup. An operator threads the patch web material 40 through the machine to the patch applicator 105. The operator then initiates the automatic threading routine by using the HMI 115. The HMI 115 is coupled to the PLC 103 and the PLC 103 controls the patch applicator 105, patch cutter 41, vacuum roll 42, and patch reject conveyor 107. A first number of patches 46 are cut by the patch cutter 41 and culled via the patch reject conveyor 107. The culled patches 46a may be a predetermined number from the start of the threading routine, or cut patches 46 could be inspected by a visual inspection station 101, and culled until the patches 46 meet visual inspection parameters 108, as seen in FIG. 3.

Also, if the machine was shut down or paused with existing patch web material loaded through the patch cutter, but a vacuum remains drawn through the vacuum anvil drum, the patch web material on the vacuum anvil drum will act as an air filter. The longer the patch web material is on the drum, the dirtier it will get. Such soiled material may not be used in the construction of products for sale. Therefore, the PLC 103 could provide a software routine for clearing the vacuum anvil drum of soiled web material. Patches that have been on the anvil for a predetermined amount of time, and therefore may have dust built up, are culled through the reject prior to machine startup. Like the automatic threading routine, a predetermined number of patches may be culled, or the patches may be inspected for dust build-up.

In addition to threading and anvil clearing, a placement accuracy routine could be provided, for use on machine startup, or when the product configuration is changed. In a representative placement accuracy routine, patches are placed to several startup reject products, and relevant dimensions are taken by a visual inspection station 101 placed downstream from the patch applicator 105. The inspection results indicate if and when the patch placement meets specified patch placement parameters.

During machine operation, the PLC 103, through software algorithms, determines whether a patch 46 should be placed by the patch applicator 105, whether the patch 46 should be culled, or whether the web 39 should be allowed to continue to run without patch placement. A patch 46 is placed on the moving chassis web 39 only if both the patch 46 and web 39 are in condition for satisfactory placement.

After machine setup and threading of any materials, the PLC 103 begins verifying status indicators at the <application> position in memory. Generally, during machine operation, the PLC 103 controls whether a patch 46 is applied by a patch applicator 105. For each product, the PLC 103 determines the action of the patch applicator 105, the patch reject conveyor 107, and the product reject conveyor 109. For each product presented to a patch applicator 105, the PLC 103 issues one of the following commands to the patch applicator 105 and patch cutter: (1) apply patch; (2) cull patch; or (3) cull web.

The apply patch command is issued if no component part has been flagged as defective in the composite web 39 that is presented to the patch applicator 105 and the patch 46, itself, satisfies inspection parameters. When the apply patch command is issued, the vacuum anvil drum 42 remains relatively stationary while the composite web 39 having a deposited adhesive is forced by the patch applicator 105 against the patch 46. After the patch 46 is applied, the PLC awaits the arrival of the next patch attachment site or product pitch.

Figure 4:
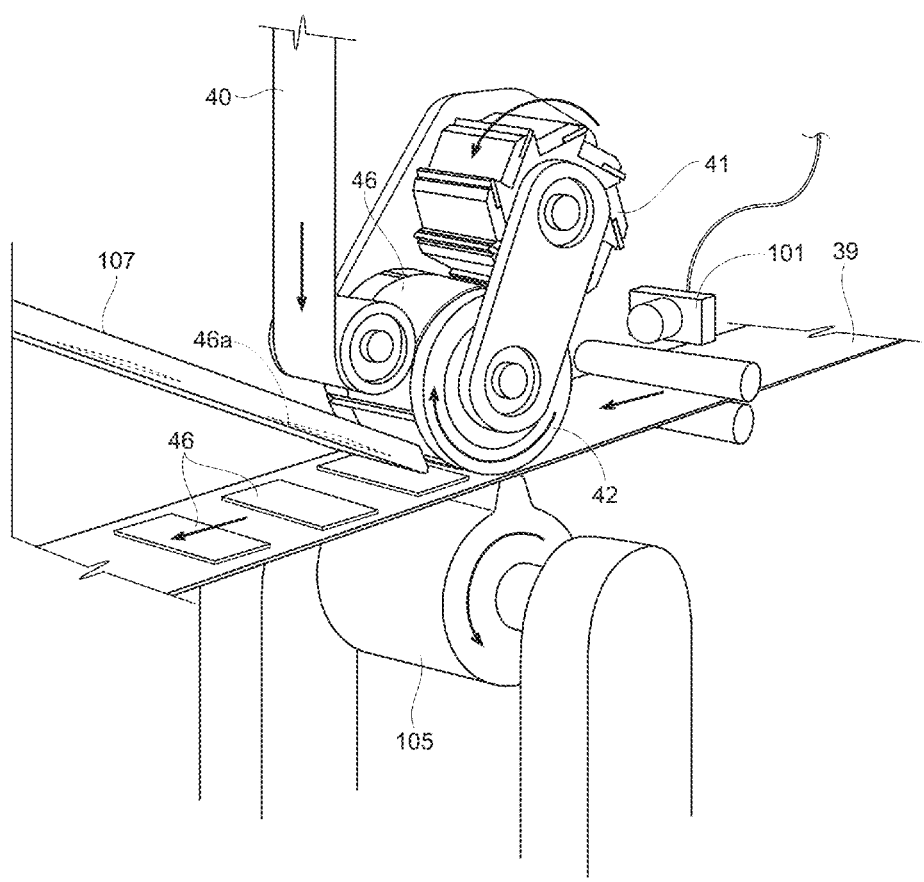
FIG. 4 is a perspective view of a patch indexer, a patch applicator and a patch reject conveyor.
Figure 5:
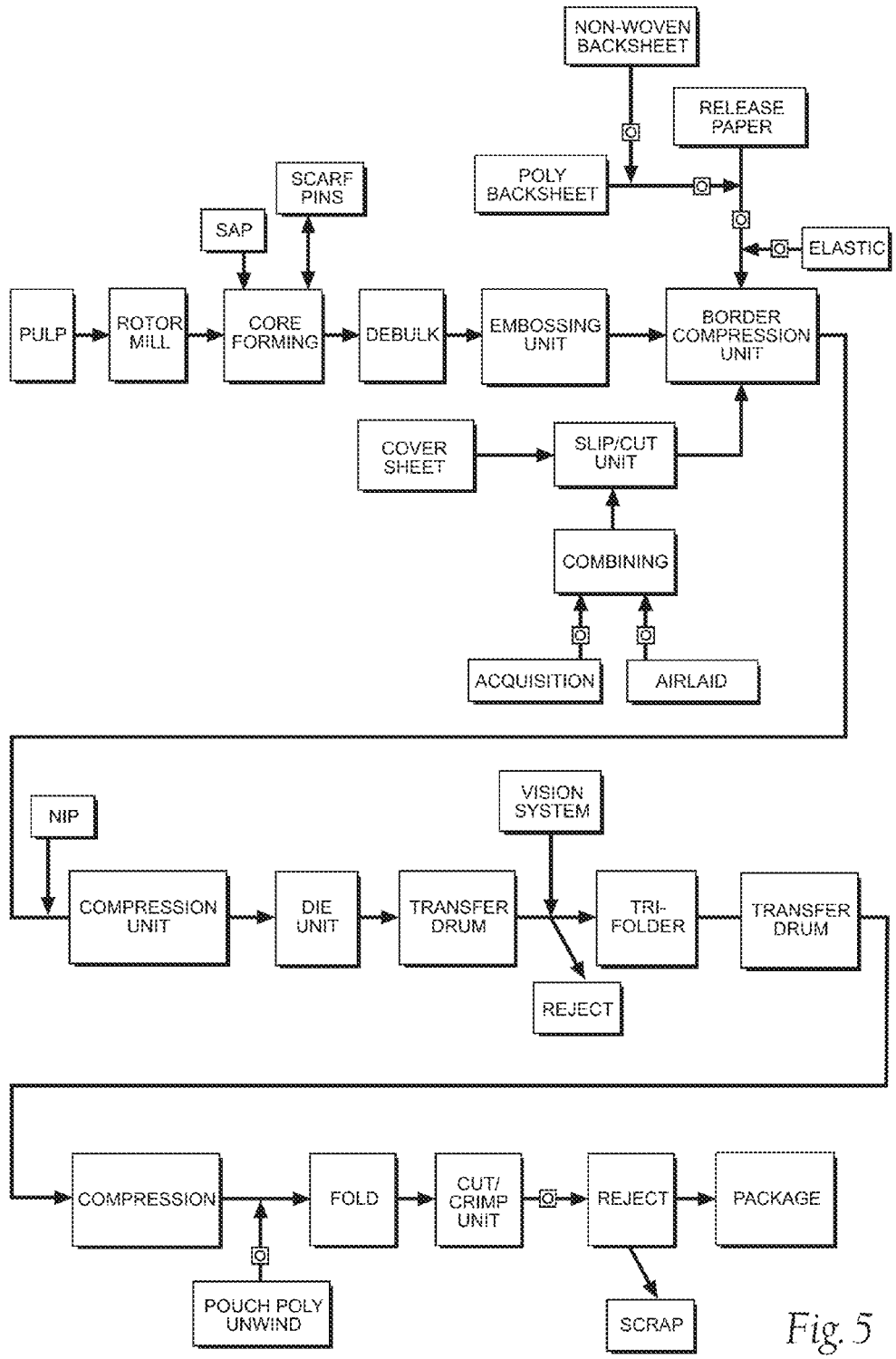
FIG. 5 is a schematic of a second embodiment of a representative web processing system.
Figure 6A:
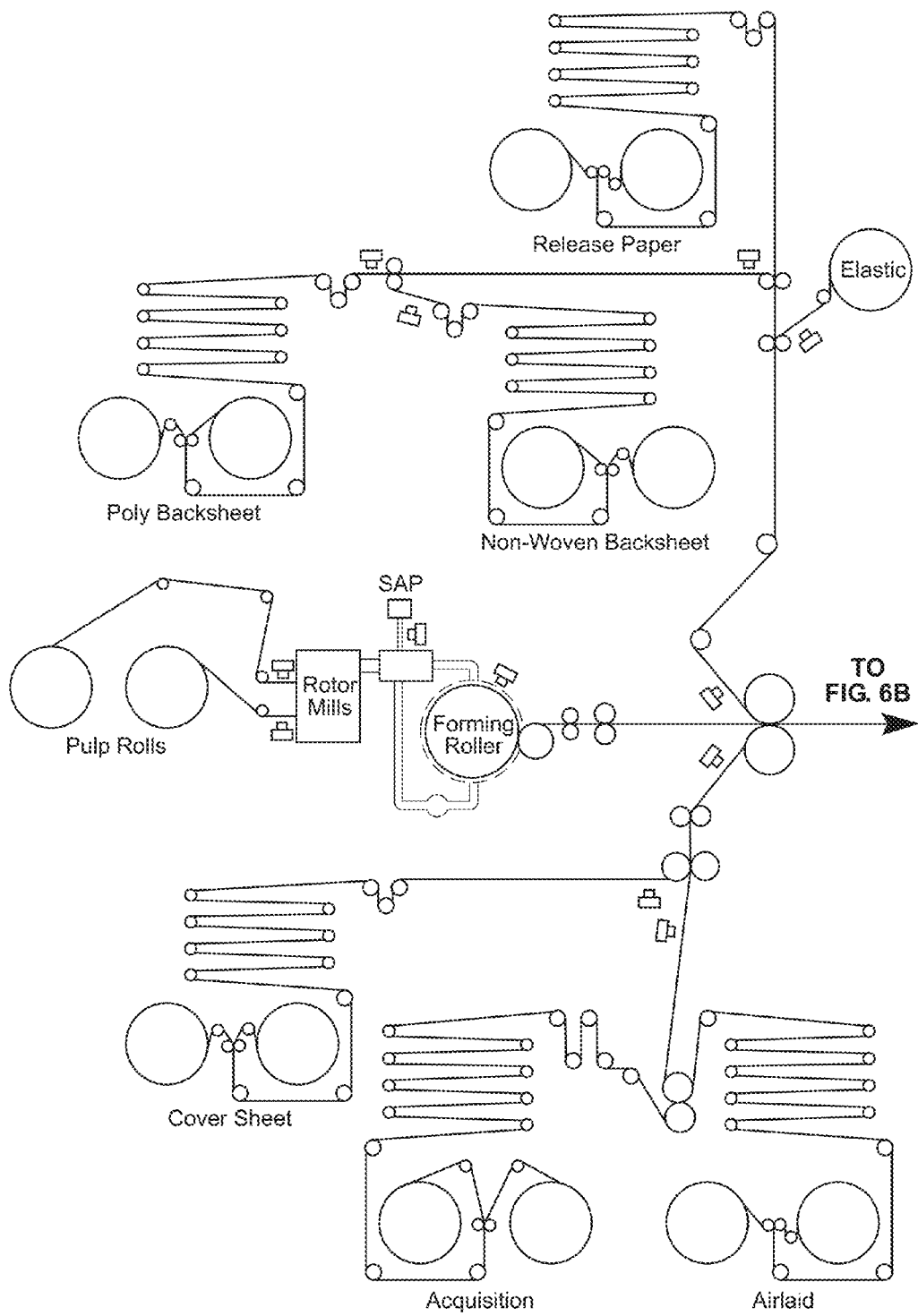
FIG. 6A-6C are additional schematic representations of a web processing system incorporating principles of the present invention.
Figure 6B:
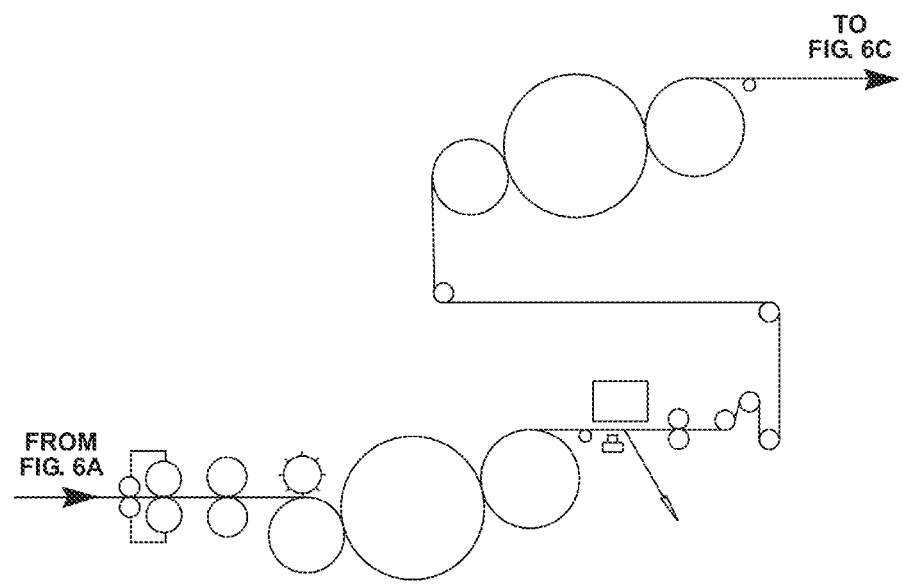
Figure 6C:
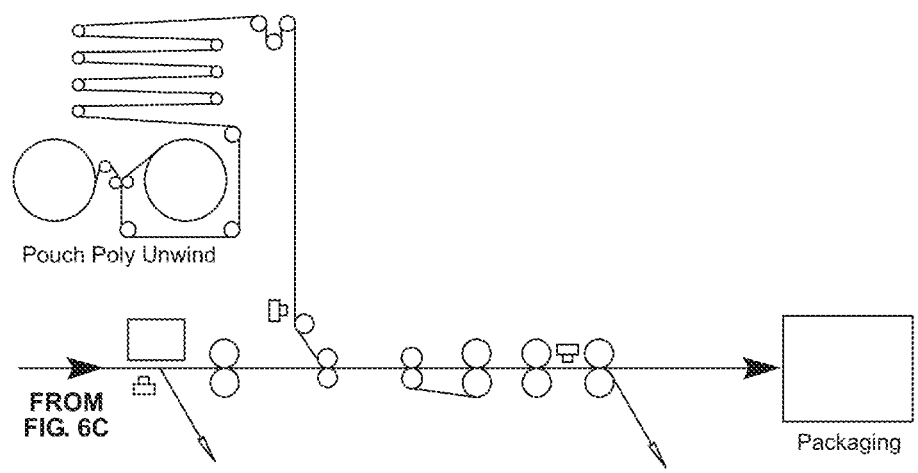

The cull patch command is issued if a patch 46a does not meet inspection parameters. Representative parameters can be seen in FIG. 4. Culling a defective patch 46a involves cooperation of the vacuum roll 42 and the patch reject conveyor 107. The vacuum roll 42 preferably has a vacuum manifold that allows a release of the vacuum draw at a certain point around the rotation path of the roll 42. The patch reject conveyor 107 may be a simple conveyor belt positioned just below the point where the vacuum draw may be removed, such that gravity causes the unapplied patch 46a to fall onto the conveyor 107.

The cull web command is issued if any component part of the composite web 39 is flagged as defective.

The PLC 103 may also contain a unit diagnostics program, which monitors parameters of the patch on the anvil to determine the health of the cutting knives and anvils. The unit diagnostics program involves the use of defined patch parameters measured by a vision inspection station and compared to expected values. Information that is gathered by the diagnostics program is stored and processed in a database. Where measured parameters are approaching acceptable limits, alerts are sent to the machine operator, indicating that potential problems are developing. The HMI may automatically present the Unit Diagnostics Screen for the operator to assess the situation. Furthermore, the HMI may provide graphics and charts to assist the operator by showing trend data, measured data, and comparable data. Thus, an operator is given advance notice of a problem so that any corrections can be made during the next machine downtime. Specifically, as the knives on the patch cutter age, the patches tend to skew. Furthermore, the deviation between subsequent patch cut lengths is another indicator that a knife blade may require replacement.

In an effort to prolong machine run-time between service and to reduce start-up rejects, an automatic anvil adjustment program may be provided. Such adjustment allows the anvil drum and knife roll to move relative to one another. Startup and shutdown rejects can result in rejections of many products. The movements are preferably in one millimeter increments over a five millimeter range. The adjustments are made as the machine is running to prevent wear on a single spot as well as to minimize buildup of cut web material on the anvil. In addition to the automatic adjustment, a manual override adjustment may be provided for troubleshooting.

If the unit diagnostics program detects a pair of patches that have parameters outside of acceptable limits, which is usually caused by a catastrophic failure of a knife or anvil, the machine operator is alerted and the HMI preferably automatically presents the Unit Diagnostics Screen for the operator to assess the situation. For every knife or anvil that fails, two patches will be affected. Therefore, if the anvil roller can accompany eight patches, twenty-five percent of the patches will fall out of acceptable limits. All patches that fall out of the acceptable limits are culled by way of the reject patch conveyor. All patches that fall within acceptable limits will continue to be placed on a composite web that is otherwise indicated as appropriate for receiving a patch. After being notified of the problem, the machine operator will observe the HMI to verify problem. In an attempt to correct the problem, the operator may try an electronic anvil shift, which, if successful, will allow the process to continue. If the electronic anvil shift does not correct the problem, the operator will request that the machine stop. To aid in repair or replacement of the failed knife or anvil, the cutter and anvil drum will stop in a position allowing easy access to the failed components. As a convenience and to enable more efficient repair of the failed components, a rapid change out (RCO) tool or kit could be provided, such as a set of hex wrenches. The operator changes the failed part and prepares the machine to restart. The routine for automatically clearing the anvil drum may then run, and the unit begins attaching patches to the composite web. The alarm that first alerted the operator of the problem is then reset, either automatically, or manually by the operator through the use of the HMI.

There may arise a situation where multiple anvils or knives appear to have failed. In this situation, the operator is alerted to the problem, but no patches are culled. Rather, a visual inspection station downstream from the patch applicator is examined to determine if there truly is a problem. If the problem is verified by the placement accuracy check, the operator shuts down the machine and proper maintenance is performed. If an examination of the placement accuracy inspection station does not confirm the purported problem, the unit diagnostics program may be suspended until it can be repaired.

Referring now to FIGS. 5 and 6*a*-*c*, an additional embodiment of a representative web processing system is shown schematically and incorporating principles of the present invention. It is noted that throughout the web processing, inspection systems can be incorporated virtually anywhere, particularly at locations of raw material input into the process.

AUTOMATED DEFECT DETECTION, ELASTIC THREADING AND RE-THREADING

FIGS. 7-15 generally describe a waste minimization technique wherein system shutdown is eliminated by first detecting a defect in a web component of a disposable product, then sequentially repairing the defect during operation of web processing machinery. The repair can be done why the machine as a whole continues operation, with a minimal number of products scrapped just prior to, during and just following the repaired portion of the web component.

Elastic laminates can be formed of a layer of stretched elastic between two non-stretched layers of non-woven material. Once the stretched elastic layer is bonded with the non-stretched non-woven, a stretch engine is formed once the elastic material is allowed to relax, forming a laminate that can be stretched in the machine direction.

Figure 7:
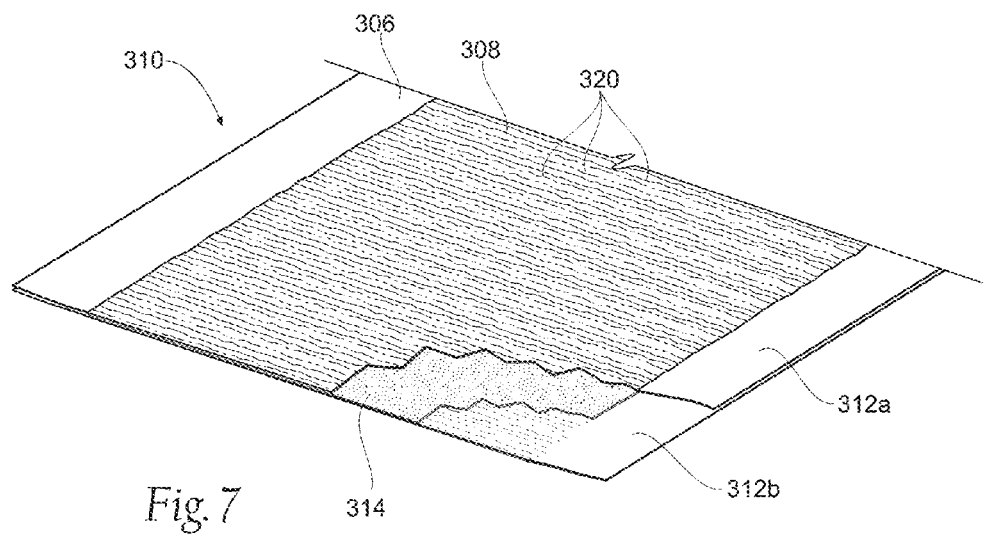
FIG. 7 is a perspective view of a layered stretch bond laminate, with an elastomeric layer sandwiched between two non-elastomeric layers of material.

Referring now to FIG. 7, a perspective view of a layered stretch bond laminate 310 is shown, with an elastomeric layer 314 sandwiched between two non-elastomeric layers 312*a* and 312*b*. A plurality of bond sites 320 are provided about an elasticized area 308, and the stretch bond laminate 310 can also be provided with a non-elasticized area 306. The non-elasticized area 306 is a preferred location for bonding the stretch bond laminate 310 to other portions of a diaper product, as the elasticized area 308 is characterized by a soft, yet discontinuous topography due to the presence of gathered areas in the elasticized area 308.

Figure 8:
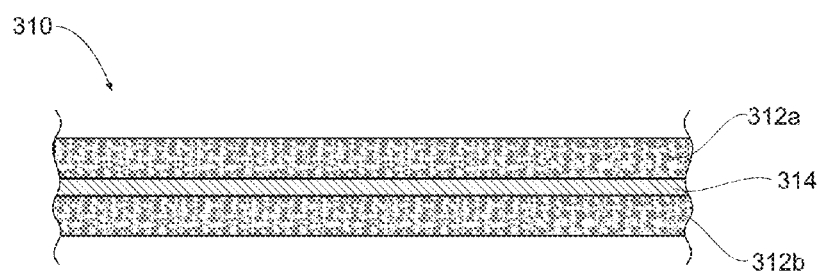
FIG. 8 is a cross-sectional view of the laminate shown in FIG. 7.

Referring now to FIG. 8, a cross-sectional view of the laminate 310 shown in FIG. 7 is shown. This view shows that the elastomeric layer 314 is sandwiched between the non-elastomeric layers 312*a* and 312*b*. In preferred embodiments, the elastomeric layer 314 can comprise a single layer, or can itself comprise a series of elastomeric materials laminated or provided together, depending on the desired elastic characteristics of the finished laminate 310.

Figure 9:
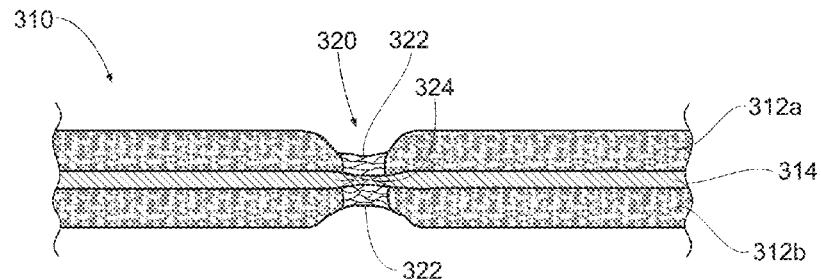
FIG. 9 is a cross-sectional view of the laminate shown in FIG. 7, with a bond-site shown.

Referring now to FIG. 9, a cross-sectional view of the laminate 10 shown in FIG. 7 is shown, with particular emphasis on a typical bond-site 320. It is preferred that the elastomeric layer 314 be chosen with good resistance to heat bonding or to ultrasonic bonding, such that when the laminate 310 is processed, the elastomeric layer 314 would behave predictably and consistently at bond sites 320. Particularly, an elastomeric layer 314, if itself formed of a lamination of several layers (not shown) can be provided, the different layers of the elastomeric layer 314 can be designed to remain somewhat intact through bond site 320. By providing a multi-layered elastomeric layer 314, the degree of flexibility in intended use, and control over reaction to heat, adhesive, or ultrasonic bonding at bond sites 320 can be more closely controlled and predicted.

As can be seen, on a microscopic level, fibrous elements 322 of non-elastomeric layers 312*a* and 312*b* remain in bond sites 320. Further, at least a portion of the elastomeric layer 314 can remain commingled with fibrous elements 322 at the bond sites, in order to provide a smooth, yet structurally stable bond at the bond site 320.

Figure 10:
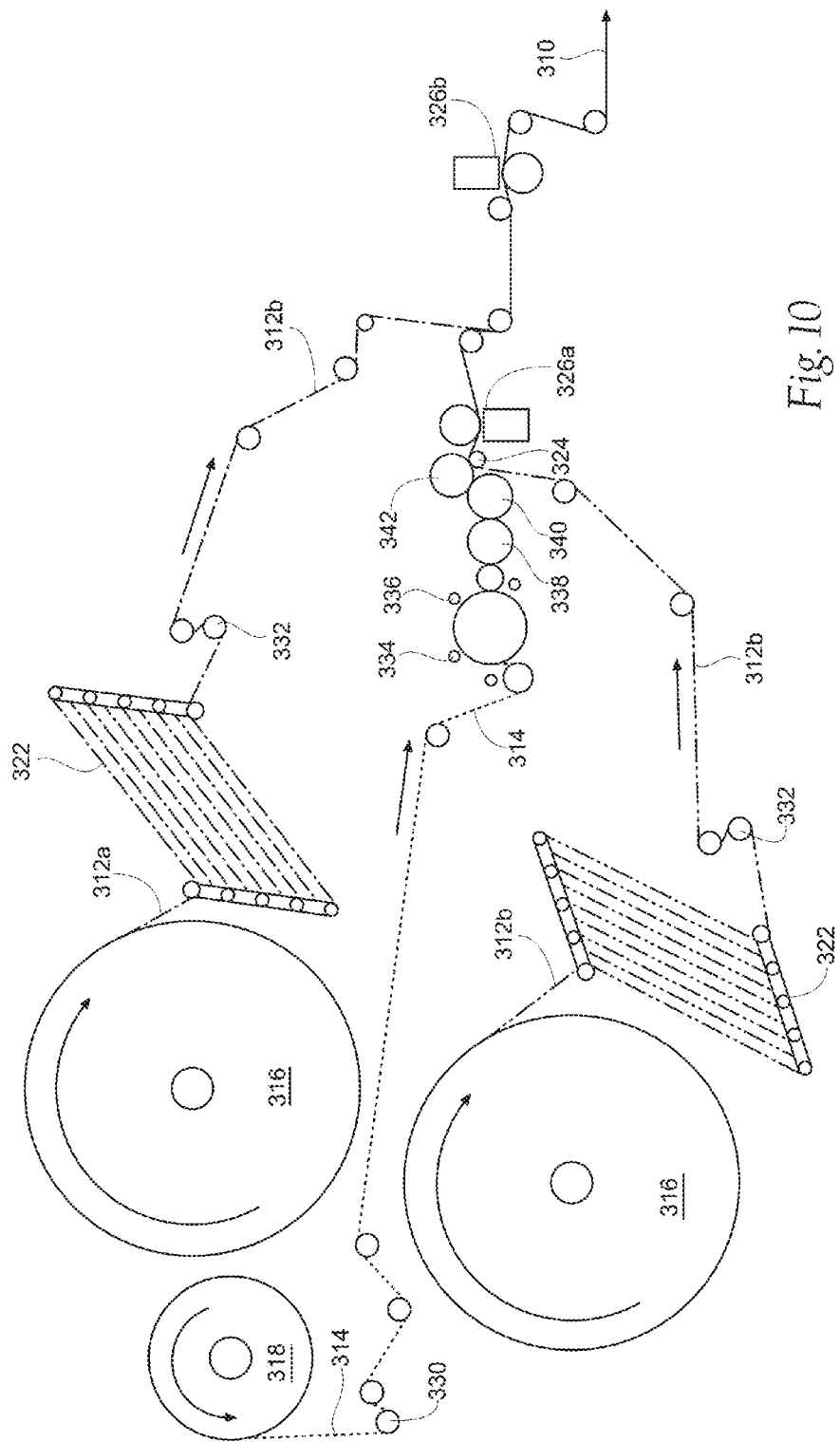
FIG. 10 is a schematic view of a two-station apparatus for forming a stretch bonded laminate.

Referring now to FIG. 10, a schematic view of a two-station apparatus for forming the stretch bonded laminate 310 is shown. Elastomeric layer 14 is unwound from drum 18 and ultimately sandwiched between the non-elastomeric layers 312*a* and 312*b*, which themselves are being unwound from primary supply wheels 316.

The unwinding process preferably incorporates web accumulator device 322. A common use of a web accumulator 322 is where a web is fed from primary supply wheel 316*s* and it is necessary to splice the leading edge of the webs 312*a* or 312*b* from a standby supply wheel (not shown) to the trailing edge of the webs 32*a* and 12*b* from the primary supply wheel 316 in a manner that will not cause interruption of the web supply to a web consuming or utilizing device.

In one known type of accumulator, the swinging dancer arm type, there is a set of spaced apart rollers on a swingable dancer arm cooperating with another set of rollers on an arm that may be stationary or swingable. A web is looped back and forth between the sets of rollers on opposed arms in a serpentine fashion. When the swingable arm is swung away from the other arm a substantial length of web is accumulated. During normal running of the web the arms will be urged to their maximum practical separation from each other to accumulate the maximum length of web. If the infeed web is slowed or stopped for a short time the tension in the web urges the arms to the minimum separation position in order to make the accumulated web available to the machine. After infeed to the accumulator is resumed the arms separate again and return to their original position to accumulate and store another length of web.

In another known type of accumulator, the linear sliding carriage type, there is a set of rollers mounted on a movable carriage which can run linearly toward or away from a set of corresponding rollers which may either be stationary or similarly slidably mounted. During normal operation of the accumulator, the two sets of rollers will be slid to their maximum practical separation to accumulate the maximum amount of web. If the infeed supply to the web accumulator is slowed or stopped, the rollers will be slid toward each other to allow the stored web to be paid out. As the web infeed is returned to regular operational speed the movable rollers slide back toward the original position to accumulate another length of web. Metering stations 332 can be provided to analyze the speed of the infeed of the layers 312*a* and 312*b*, and to assist in determining how much material remains on infeed rolls.

Referring still to FIG. 10, a blocking isolation s-wrap 330 can be provided for carrying and tensioning elastomeric layer 314. Elastomeric layer 314 enters a first cross machine direction stretch wheel 334 on one side of the web 314 in the direction of travel, and then a second cross machine direction stretch wheel 336 on the other side of the web 14 in the direction of travel. First, second and third stretch rollers 338, 340, and 342 are provided. In conjunction with the stretch wheels 334 and 336, and the stretch rollers 338, 340 and 342, the elastomeric layer 314 is stretched in a direction and tension that is user defined based on preference of the elasticity of the lamination 310. It is noted that stretching can be supplied to elastic layer 314 in any of the cross machine direction, the machine direction, or a combination of both, depending on the desired end result.

A first ultrasonic bonding station 326*a* achieves breathability by joining the non-elastomeric layer 312*b* with the stretched elastomeric layer 14. Because the elastomeric layer 314 has been stretched, yet the non-elastomeric layer 312*b* has not been stretched, when the two layers are joined, the elastomeric layer 314 still will have stored the stretch.

Next, the second ultrasonic bonding station 326b bonds the pre-bonded combination of the non-elastomeric layer 312b and elastomeric layer 314 with the non-elastomeric layer 312a, achieving thee elastic lamination 310. Next, the elastomeric layer 314 is taken off of tension, which results in a gathering of the elastomeric layer 314 to create the ripple like appearance of the material as seen in FIG. 7.

One advantage of two station bonding is that it offers flexibility for different anvil patterns at each station. For instance, a chicken feet pattern at the first station 326a, and a dot pattern anvil at the second station 326b, results in good breathability as well as good elastic retention forces at smaller bond sites. Additionally, because ultrasonic bonding station 326a is not required to penetrate three layers 312a, 314 and 312b, flexibility is offered with the degree of energy supplied.

Figure 11:
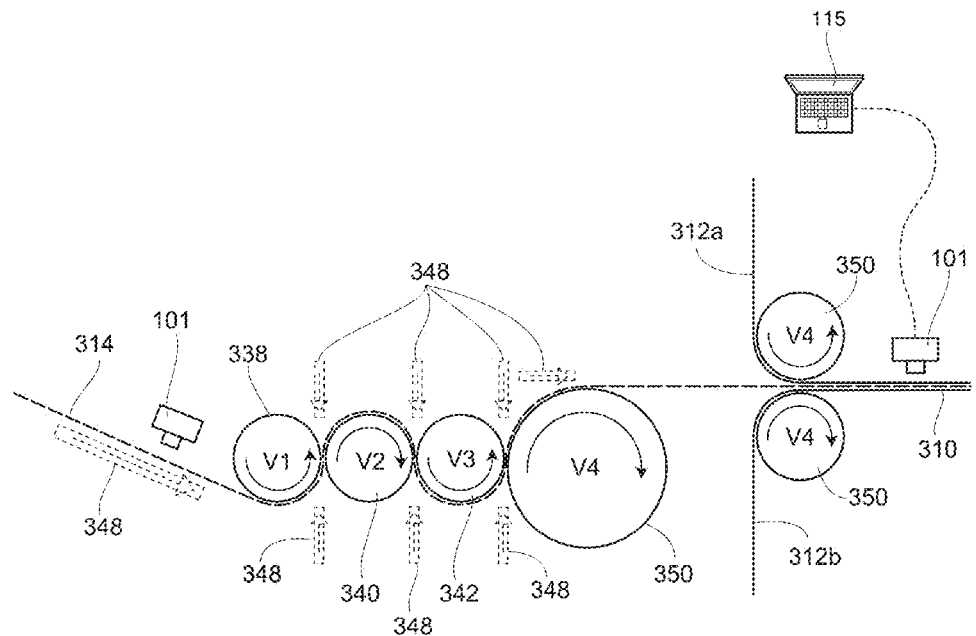
FIG. 11 is a schematic view of an apparatus for forming a stretch bonded laminate, the apparatus equipped with a series of air knives to urge an elastic layer in the machine or the reverse machine direction through a stretch wheel array.

Alternatively, the two non-woven layers 312a and 312b can be brought together with the elastomeric layer 314 sandwiched between, and the elastomeric layer 314 can be bonded to both non-woven layers 312a and 312b simultaneously (see FIG. 11). This has the advantage of only requiring one bonding station.

During construction of such laminates, defects in the elastic material 314 supplied to the process can result in snapped or otherwise unacceptable elastic introduced to the laminate. If such unacceptable elastic is introduced into the laminate, the manufacturing process can require slowing or stoppage in order for properly produced laminate to be re-introduced into the process and rethreaded in the manner shown in FIG. 11. One aspect of the present invention relates to an automated method and apparatus to first detect such defects, and to automatically re-thread the elastic material through stretch rollers and continue with the processing sequence using acceptable elastic material resulting in an acceptable formed laminate.

Such automation results in less manual threading and re-threading, less system downtime, and and scrapped product resulting from unacceptable elastic forming unacceptable laminate being present in finished product.

Air knives (shown schematically on FIG. 11) are used in the procedure described below in order to urge and thread the elastic layer through stretch rollers in the machine direction as will be described later. Air knives are also used, when necessary, to reverse defected elastic layers in reverse machine direction back out of the stretch rollers, and then again forward in the machine direction through the stretch rollers in the machine direction in order to continue the laminate construction.

An air knife, such as a commercially available EXAIR air knife, is a tool traditionally used to blow off liquid or debris from products as they travel on conveyors. The knife consists of a high intensity, uniform sheet of laminar airflow.

A pressurized air plenum containing a series of holes or continuous slots through which pressurized air exits in a laminar flow pattern characterizes an air knife. The exit air velocity then creates an impact air velocity onto the surface of whatever object the air is directed. This impact air velocity can range from a gentle breeze to greater than Mach 0.6 (40,000 ft/min) to alter the surface of a product without mechanical contact.

Traditional uses of air knives remove liquids, control the thickness of liquids, dry the liquid coatings, remove foreign particles, cool product surfaces or create a hold down force to assist in the mechanical bonding of materials to the surface. The present use of an air knife to transport a loose end of a web material, such as an elastic material is novel. Several air knives are used in succession to guide or thread the loose end of the web material through a series of rollers or in another targeted direction.

Referring now to FIG. 11, a system for threading and re-threading the elastic layer 314 into the stretch wheels 338, 340, 342 and 350 is shown. Stretch wheel 338 travels at the infeed velocity V1 to mach the speed of the incoming elastomeric layer 314. Next, stretch wheels 340, 342 and finally 350 operate at successively faster velocities V2, V3 and V4. V4 is preferably the same speed as incoming non-woven layers 312a and 312b. An air knife 348 is positioned between the incoming web of elastomeric layer 314 and the first stretch wheel 338. A series of air knives 348 are provided at additional downstream locations where it is desired to steer the elastomeric layer 314.

Referring still to FIG. 11, the system is shown in its operating condition, with incoming elastomeric 314 already threaded under stretch wheel 338, over stretch wheel 340, under stretch wheel 342, and finally over stretch wheel 350. The air knives 348 are all shown in phantom on FIG. 11, indicating that air is not being directed through the knives 348, because under normal operating conditions, the air is not necessary to steer the threaded elastic 314. However, should the elastic 314 become deformed or snap, the elastic 314 will need to be re-threaded in the manner shown in FIG. 11 to resume system operation.

If the elastomeric layer 314 should be detected as being unacceptable, a threading/re-threading sequence is initiated. Unacceptable elastomeric 314 infeed conditions can be indicated for instance by the first camera positioned near the infeed of elastomeric layer 314; or missing elastomeric, as determined by the next camera positioned after the non-woven layers have been sandwiched about the elastomeric layer 314; or by a pressure sensor mounted before the first stretch wheel 338.

Depending on the location and nature of the free end of the incoming elastomeric 314, which can be determined by additional vision sensors deployed throughout the stretch wheel array, the elastomeric 314 might require retreatment from the stretch wheel array (for instance if the free end of the incoming elastomeric 314 is within the stretch wheel array). Alternatively, if the free end of the incoming elastomeric 314 is prior to the first stretch wheel 338, retreatment will not be necessary.

The threading/re-threading sequence involves nearly immediate movement of the first and third stretch wheels 338 and 342 (see FIGS. 17 and 18) in order to provide adequate space for the elastomeric 314 to be threaded through all of the stretch wheels, which, in their operating condition, are spaced closely together.

Figure 12A:
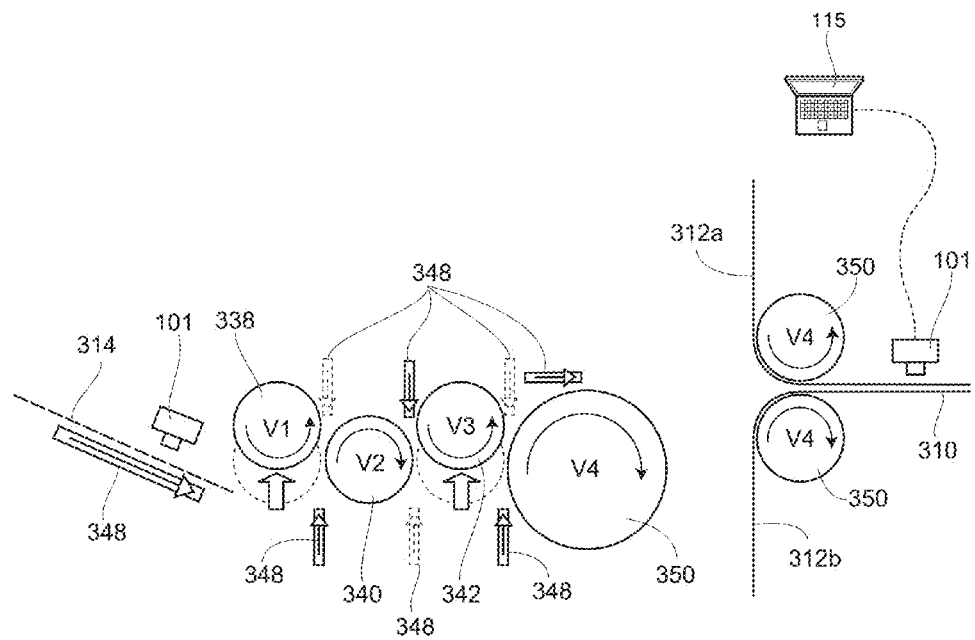
FIGS. 12A-C are schematic views of the apparatus shown in FIG. 11, operating in a threading sequence to thread the elastic layer through the stretch wheel array.
Figure 12B:
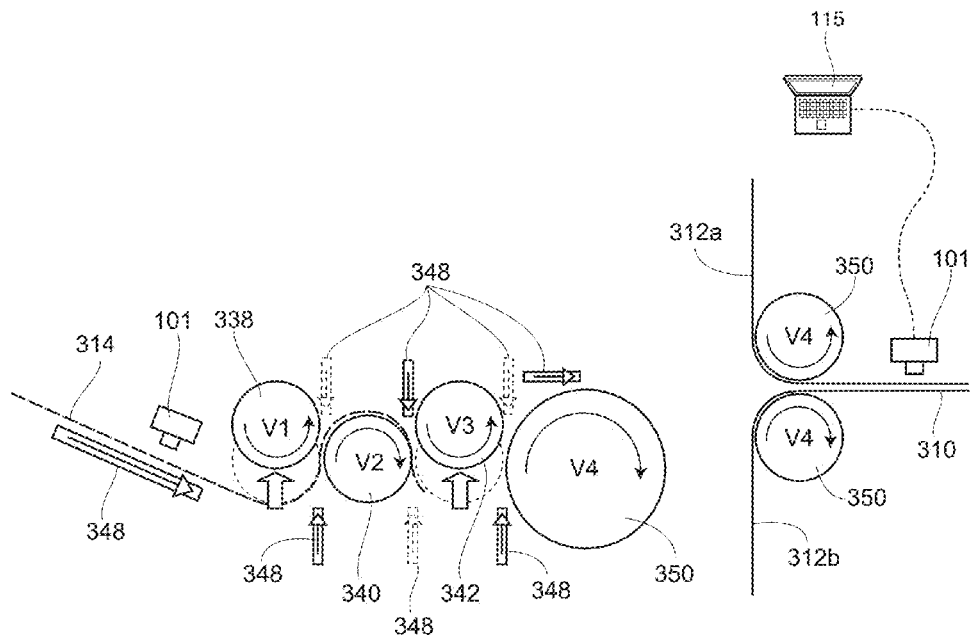
Figure 12C:
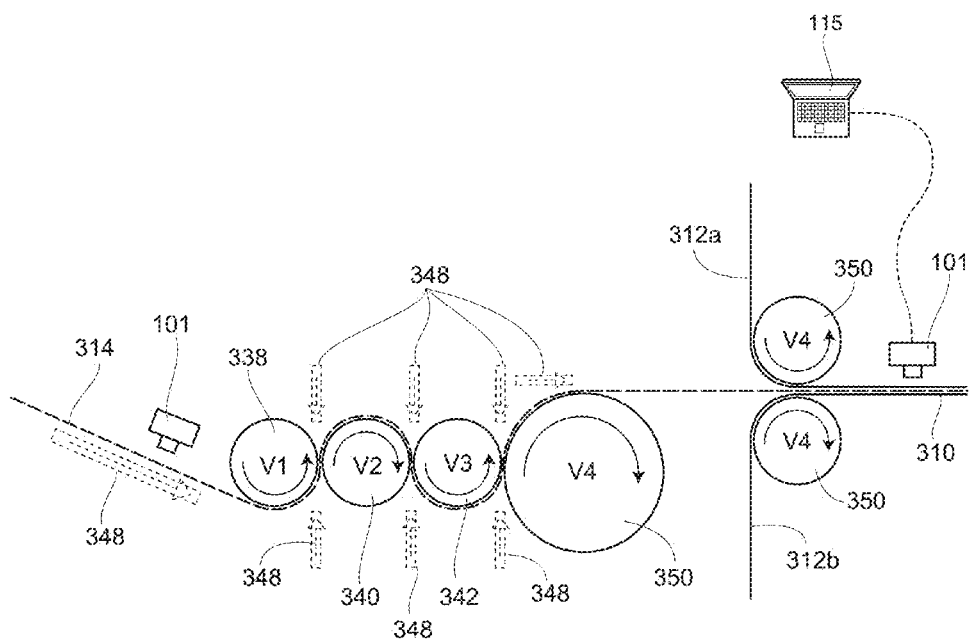

Referring now to FIGS. 12A-12C, if the free end of the incoming elastomeric 314 is prior to the first stretch wheel 338, retreatment will not be necessary, and the threading sequence is shown. As can be seen, the air knives 348 indicated in solid lines are activated with air advancement shown in the machine direction. The first air knife 348 (shown at left) advances the leading edge of the incoming elastomeric 314 being paid in at its V1 velocity, by urging the laminar air flow at the leading edge. The second activated air knife 348 directs more laminar air flow at the leading edge of the elastomeric 314 to urge the leading edge of the elastomeric 314 between the void created by the separated stretch wheels 338 and 340. The third activated air knife 348 directs the leading edge of the elastomeric 314 to urge the leading edge of the elastomeric 314 between the void created by the separated stretch wheels 340 and 342 (see FIG. 12b). The fourth activated air knife 348 directs the leading edge of the elastomeric 314 to urge the leading edge of the elastomeric 314 between the void created by the separated stretch wheels 342 and 350. The last activated air knife 348 directs the leading edge of the elastomeric 314 to urge the leading edge of the elastomeric 314 between the non-woven layers 312a and 312b (FIG. 12c). At this point, the first and third stretch wheels 338 and 342 are returned to their operating spacing, the activated air knives 348 are deactivated, and the system is restored to its original and properly functioning operating condition, identical to shown in FIG. 11.

Figure 13:
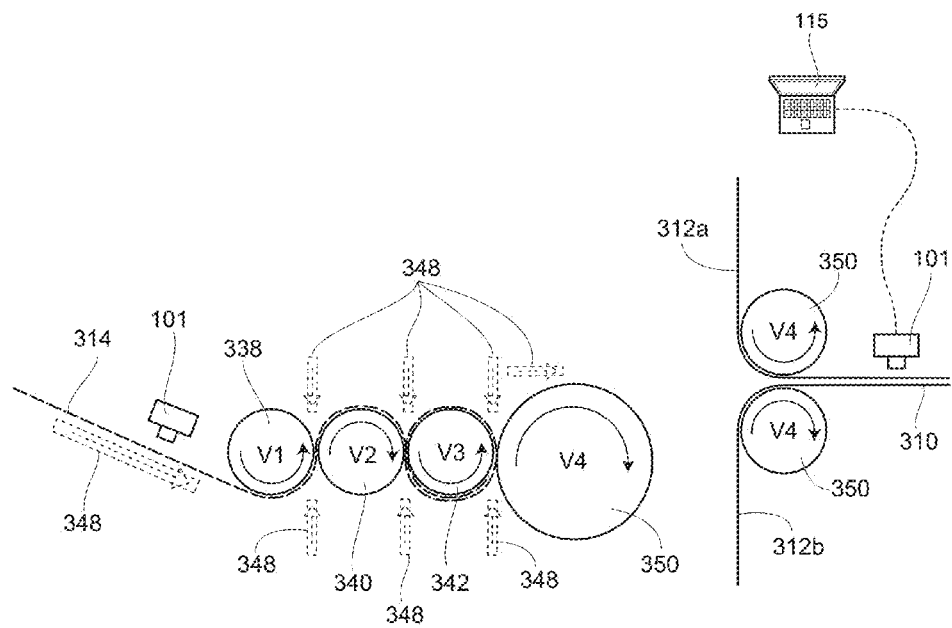
FIGS. 13-15 are schematic views of the apparatus shown in FIG. 11, operating in an unthreading or retreating sequence to unthread the elastic layer through the stretch wheel array, after which the machine will operate in the threading sequence shown in FIGS. 12A-C.
Figure 14:
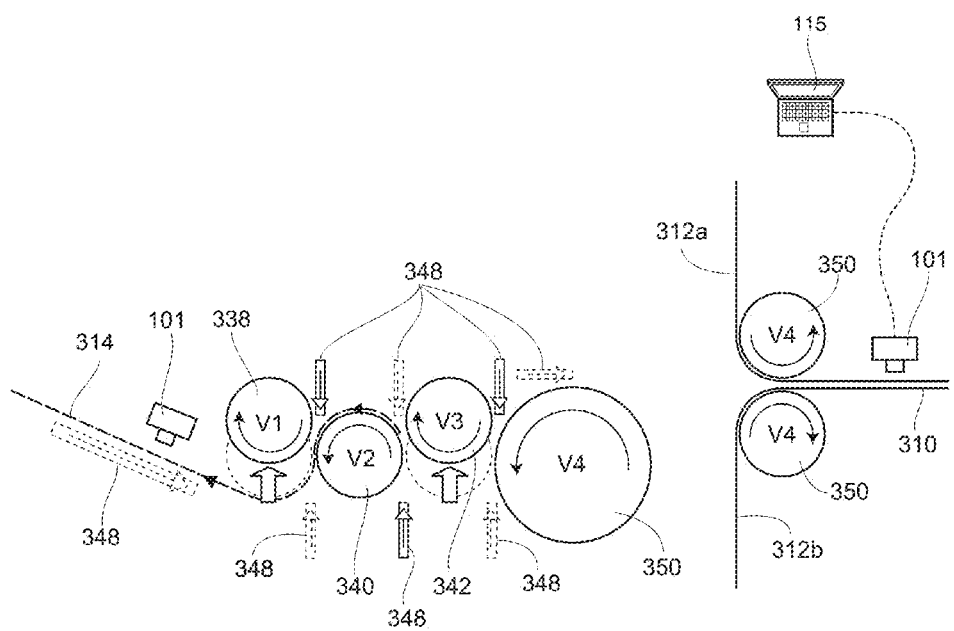
Figure 15:
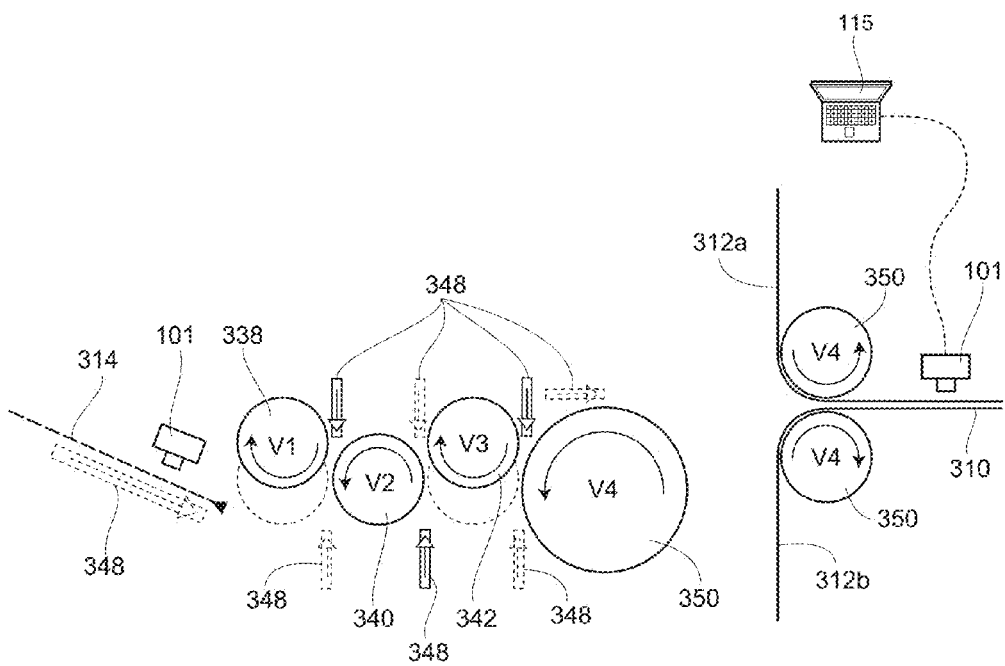

Referring now to FIGS. 13-15, if the system, through pressure sensors or vision sensors deployed throughout the stretch wheel array has determined that the free end of the incoming elastomeric 314 is within the stretch wheel array (in the illustrated embodiment, about stretch wheel 342 in FIG. 13, a retreatment and threading/rethreading sequence is initiated as shown in FIGS. 13-15. In this sequence, there is also nearly immediate movement of the first and third stretch wheels 338 and 342 as shown in FIG. 14 (see also FIGS. 17 and 18) in order to provide adequate space for the elastomeric 314 to be retreated and then threaded through all of the stretch wheels as previously described. In the retreatment sequence, the air knives 348 shown in bold are activated in order to urge the leading edge of the elastomeric 314 in the reverse machine direction, retreating upstream of the machine direction. The upstream facing air knives 348 remain activated until it is detected that the leading edge of the elastomeric 314 has been removed from the stretch wheel array (see FIG. 15). When the first camera (left side of FIG. 15) detects the leading edge of the elastomeric 314, the threading sequence as described in FIGS. 12A-12C is activated until the system continues in its normal operating condition of FIG. 11.

Figure 16:
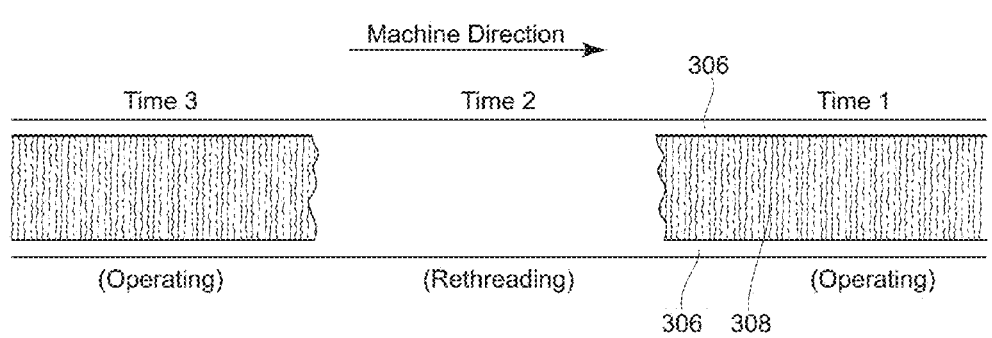
FIG. 16 is a plan view of a laminate formed during operating and threading/rethreading periods, with the laminate having elastic in the laminate during the operating timeframes, and no elastic in the threading/rethreading time periods.

Referring now to FIG. 16, because the threading or the retreating/threading sequences operate while the non-woven layers 312a and 312b are still being introduced, there exists a gap in the introduction of the elastomeric layer 314 between time 1, the initially operating timeframe and time 3, the operating timeframe after rethreading has taken place (time 2). Material produced during time period 2, during which threading (and possibly retreatment/threading) will not have the elastomeric layer 314 introduced. Material produced during time period 2 will therefore be unacceptable for use in final product. Depending on user preference, the non-elastic laminate produced during time period 2 can still be introduced into downstream products such as diapers, with those products being discarded by the logic system after final production. Alternatively, the logic system can temporarily halt introduction of other diaper components at times downstream matching up with when the non-elastic laminate produced during time period 2 would have been introduced with other components.

Figure 17:
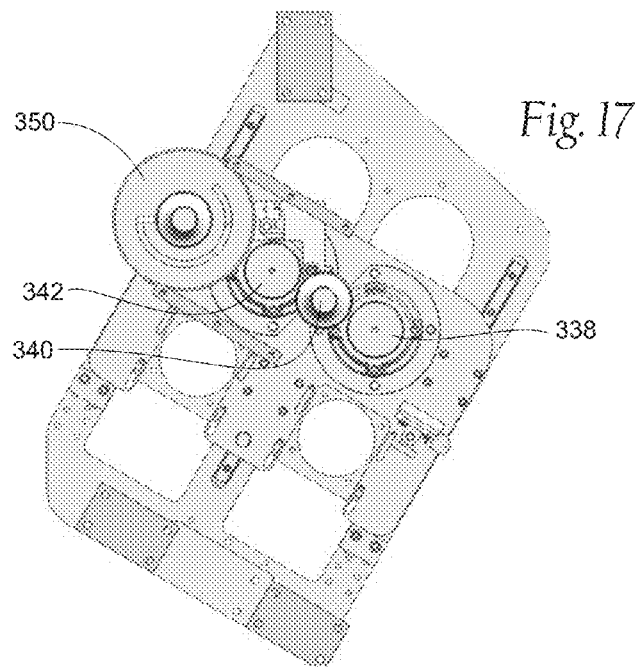
FIGS. 17 and 18 are a drive-side view of the stretch wheel array operating in a closely spaced operating position (FIG. 17) and a spaced apart, threading/unthreading position (FIG. 18).
Figure 18:
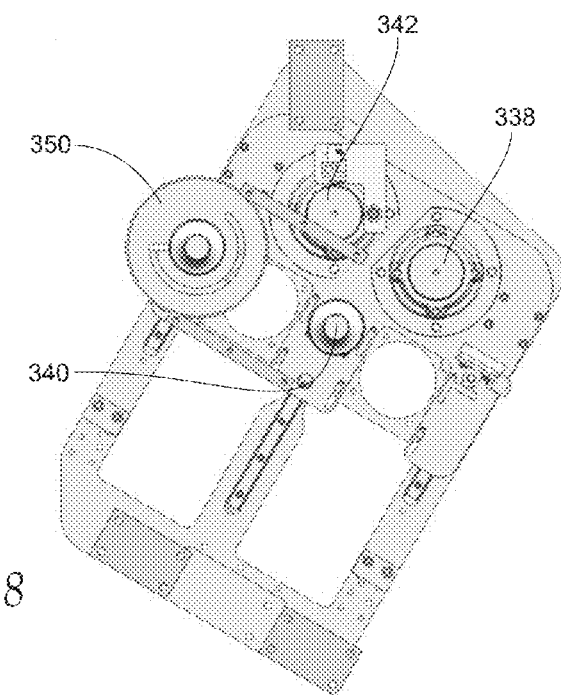

Referring now to FIGS. 17 and 18, a drive side view of the stretch array 338, 340, 342, and 350 is shown. In the operating condition shown in FIG. 17, the components are in their closely spaced configuration (see FIG. 11). In the spaced apart condition shown in FIG. 17, the stretch wheels 342 and 338 have been moved linearly away from the stretch wheels 340 and 350 to allow the spacing between stretch wheels adequate for the air driven threading operation.

Although the foregoing description involves the placement of an absorbent insert or patch onto a diaper chassis, it will be apparent to those skilled in the art that the apparatus and process could be used to avoid unnecessary waste in the application of any sort of patch to a moving web. Other examples of patches that may be placed are tape tab patches and reusable fasteners.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

We claim:
1. An apparatus for threading a material layer through a machine path, the apparatus comprising a forwarding series of blowing air mechanisms aimed at said material layer in a machine direction to guide said material layer in said machine direction forwards through said machine path until an acceptable material state is achieved; a sensor; and a reversing series of blowing air mechanisms aimed at said material layer in a reverse machine direction to guide said material layer in said reverse direction; said sensor operatively coupled with said forwarding series of blowing air mechanisms and operatively coupled with said reversing series of blowing air mechanisms; at most one of said forwarding series of blowing air mechanisms and said reversing series of blowing air mechanisms instantaneously operative upon said material layer.

\* \* \* \* \*